(12) United States Patent
McGahan et al.

(10) Patent No.: US 10,231,761 B2
(45) Date of Patent: *Mar. 19, 2019

(54) SURGICAL TOOL

(71) Applicant: Warsaw Orthopedic, Inc, Warsaw, IN (US)

(72) Inventors: Thomas V. McGahan, Germantown, TN (US); Jeetendra S. Bharadwaj, Lafayette, CO (US); Bradley E. Steele, Plymouth, MN (US)

(73) Assignee: Warsaw Orthopedic, Inc., Waesaw, IN (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/160,635

(22) Filed: May 20, 2016

(65) Prior Publication Data

US 2017/0333092 A1 Nov. 23, 2017
US 2018/0289399 A9 Oct. 11, 2018

Related U.S. Application Data

(62) Division of application No. 14/606,702, filed on Jan. 27, 2015, now Pat. No. 9,364,270, which is a division of application No. 12/609,933, filed on Oct. 30, 2009, now Pat. No. 8,974,932.

(51) Int. Cl.
| | | |
|---|---|---|
| *H01M 2/10* | (2006.01) | |
| *A61B 17/70* | (2006.01) | |
| *H02J 7/00* | (2006.01) | |
| *A61B 17/16* | (2006.01) | |
| *A61B 17/00* | (2006.01) | |
| *A61B 90/00* | (2016.01) | |

(52) U.S. Cl.
CPC ...... *A61B 17/7074* (2013.01); *A61B 17/1622* (2013.01); *A61B 17/1628* (2013.01); *A61B 17/7076* (2013.01); *H01M 2/105* (2013.01); *H02J 7/0013* (2013.01); *H02J 7/0045* (2013.01); *A61B 2017/00407* (2013.01); *A61B 2017/00734* (2013.01); *A61B 2090/0807* (2016.02); *H01M 2220/30* (2013.01)

(58) Field of Classification Search
None
See application file for complete search history.

(56) References Cited

U.S. PATENT DOCUMENTS

| | | |
|---|---|---|
| 3,886,944 A | 6/1975 | Jamshidi |
| 5,207,697 A | 5/1993 | Carusillo et al. |
| 5,792,573 A | 8/1998 | Pitzen et al. |
| 5,977,746 A | 11/1999 | Hershberger et al. |
| 6,126,670 A | 10/2000 | Walker et al. |

(Continued)

*Primary Examiner* — Wyatt P McConnell

(57) ABSTRACT

A battery pack for a use with a powered surgical tool. The battery pack may include a housing with an outer wall and opposing first and second ends. The housing may include an elongated shape that extends between the first and second ends. A first member may extend across the first end of the housing and include a first aperture, and a second end member may extend across the second end of the housing and may include a second aperture. A passage may extend through the housing with a first end that aligns with the first aperture and a second end that aligns with the second aperture. The housing may be sized for a plurality of storage locations positioned between the first and second members and around the passage, and each of the storage locations may be configured to store a power cell.

7 Claims, 34 Drawing Sheets

(56) References Cited

U.S. PATENT DOCUMENTS

| | | |
|---|---|---|
| 6,756,766 B2 | 6/2004 | Miller |
| 6,887,244 B1 | 4/2005 | Walker et al. |
| 6,917,183 B2 | 7/2005 | Barlev et al. |
| RE40,681 E | 3/2009 | Pitzen et al. |
| 7,501,198 B2 | 3/2009 | Barlev et al. |
| RE40,848 E | 7/2009 | Pitzen et al. |
| 2003/0149424 A1 | 8/2003 | Barlev et al. |
| 2003/0205987 A1 | 11/2003 | Barlev et al. |
| 2004/0012370 A1 | 1/2004 | Miller |
| 2005/0020909 A1 | 1/2005 | Moctezuma de la Barrera et al. |
| 2005/0096661 A1 | 5/2005 | Farrow et al. |
| 2005/0159752 A1 | 7/2005 | Walker et al. |
| 2007/0182369 A1 | 8/2007 | Gerber et al. |
| 2009/0181291 A1 | 7/2009 | Lewis, II et al. |

SURGICAL TOOL

CROSS REFERENCE TO RELATED APPLICATIONS

The present application claims priority to and is a divisional of U.S. patent application Ser. No. 15/094,369 filed on Apr. 8, 2016 which is a Divisional of U.S. application Ser. No. 14/606,702 filed on Jan. 27, 2015 which is a continuation-in-part of U.S. application Ser. No. 12/609,933 filed on Oct. 30, 2009 and Issued U.S. Pat. No. 8,974,932. These applications are herein incorporated by reference in their entireties.

RELATED APPLICATION

This application is a continuation-in-part of U.S. patent application Ser. No. 12/559,182 filed on Sep. 14, 2009 and herein incorporated by reference in its entirety.

BACKGROUND

Field of the Disclosure

This disclosure is directed to a surgical tool, and more particularly directed toward a surgical tool for removing a portion of an implant.

Description of the Related Art

There are a variety of different spinal diseases, such as sclerosis, as well as others, which may be cured or mitigated by implantation of certain devices. Such devices can include articles and mechanisms useful for repairing damaged portions of the spine, stabilizing portions of the spine, or changing the position of the spine to a more healthy state. For example, rod and anchor systems are commonly employed when portions of the spine need to be realigned, such as in patients with abnormal curvatures, wherein the rod provides rigid support for urging the spine to a more healthy position.

Typically, the process of implanting rod and anchor systems can be quite daunting, including the implantation of multiple anchors or bone screws within particular locations of the spine and then attaching each of the anchors to a rod. Depending upon the severity of the spinal disease and the necessary suitable treatment, such surgeries can last hours if not more. Moreover, most of the components used in the surgery are rigid components that must be physically manipulated by a surgeon while in the patient (i.e., in-situ) leading to potential physical harm to the patient as some of the procedures can result in substantial jarring of the patient including for example, shearing off the head portions of set screws for permanent placement. Additionally, such manipulation by a surgeon may also compromise the integrity of the implanted object lessening its capabilities. Given the delicacy of surgical procedures and the anatomical importance of the spine, jarring of the patient during such surgical procedures is inherently dangerous. Additionally, the vast majority of these surgical procedures are completed by handheld manual tools, meaning hours of rigorous work for a surgeon to implant all the screws and properly align the spine with an implanted rod.

SUMMARY

The present application is directed to a battery pack for a use with a surgical tool. The battery pack may include a housing with an outer wall and opposing first and second ends. The housing may include an elongated shape that extends between the first and second ends. A first member may extend across the first end of the housing and include a first aperture, and a second end member may extend across the second end of the housing and may include a second aperture. A passage may extend through the housing with a first end that aligns with the first aperture and a second end that aligns with the second aperture. The housing may be sized for a plurality of storage locations positioned between the first and second members and around the passage, and each of the storage locations may be configured to store a power cell.

DETAILED DESCRIPTION

Description of Relevant Anatomy

Figure 1:
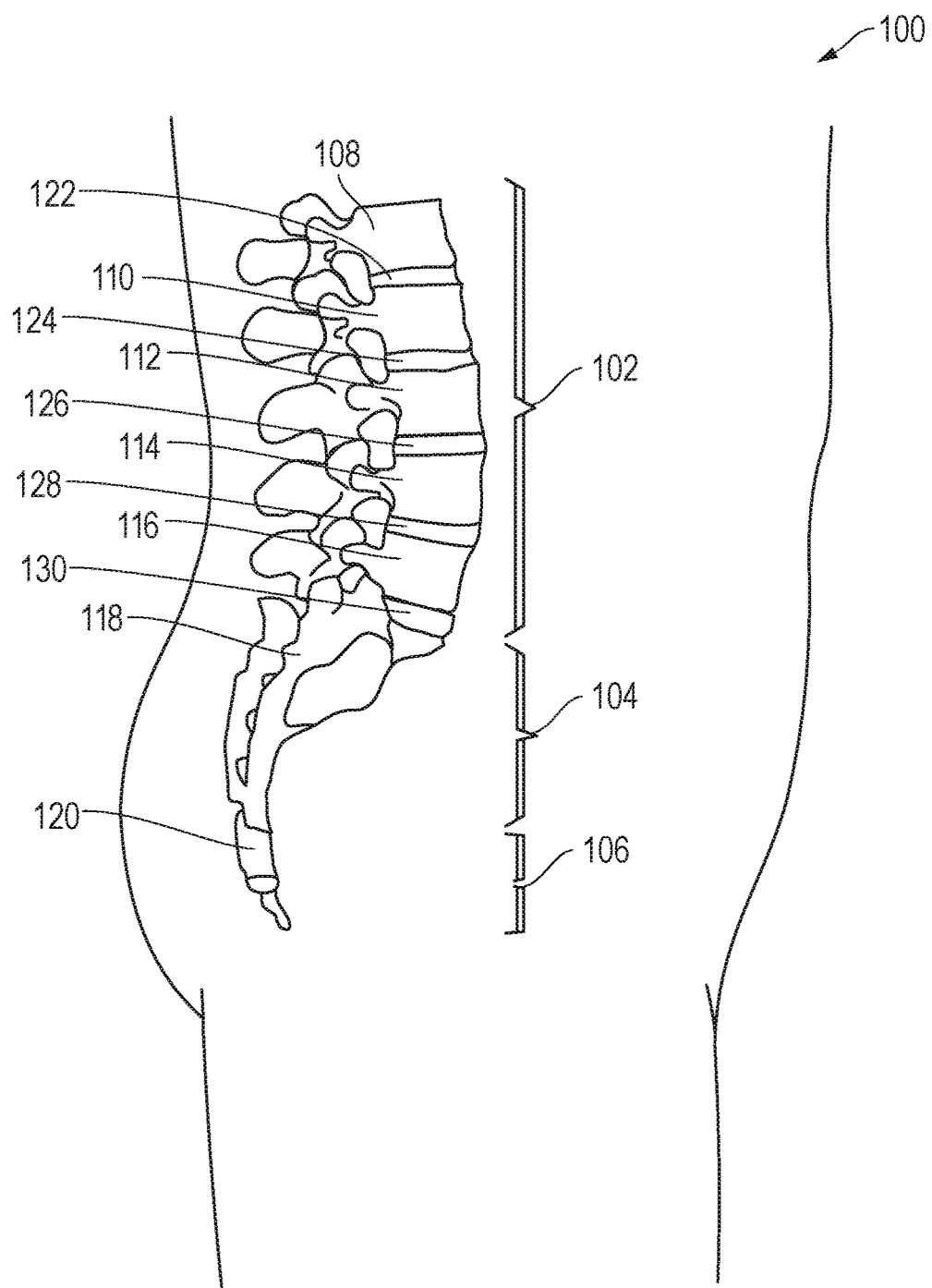
FIG. 1 includes a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114.

Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged or if one of the zygapophyseal joints is diseased, degenerated or damaged, that disc or joint can be treated with an implanted device.

Figure 2:
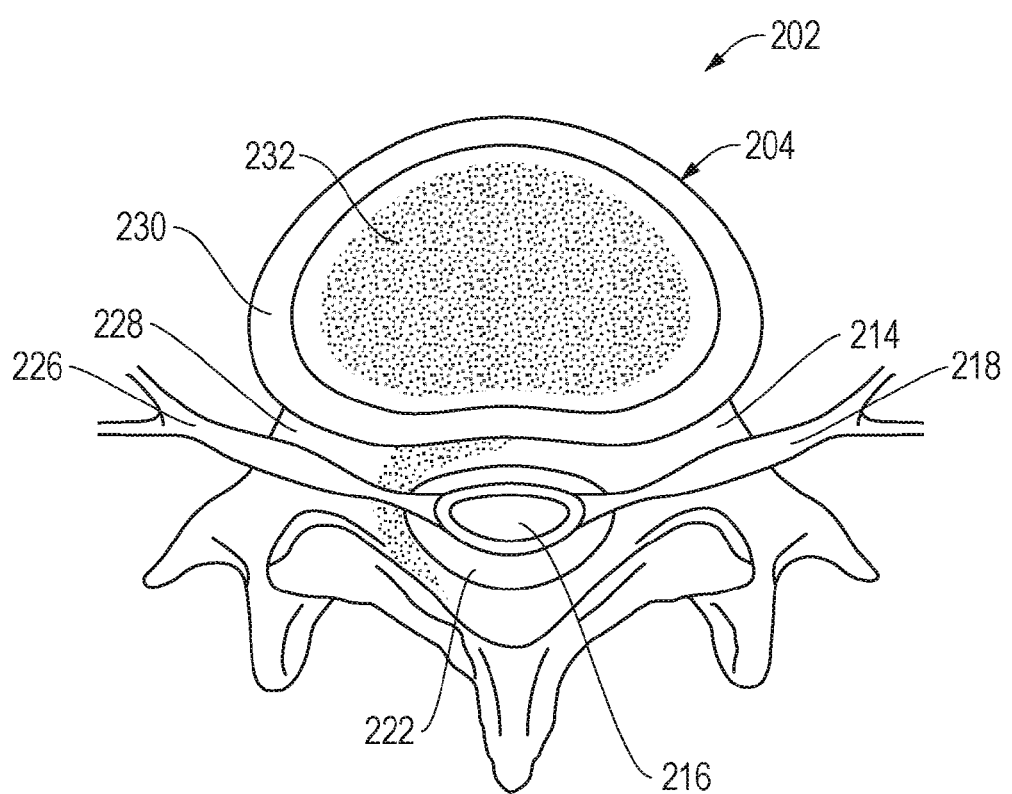
FIG. 2 includes a top plan view of a vertebra.

Referring to FIG. 2, a top plan view of a vertebra is illustrated. As shown, the vertebral body 204 of the inferior vertebra 202 includes a cortical rim 230 composed of cortical bone. Also, the vertebral body 204 includes cancellous bone 232 within the cortical rim 230. The cortical rim 230 is often referred to as the apophyseal rim or apophyseal ring. Further, the cancellous bone 232 is generally softer than the cortical bone of the cortical rim 230.

As illustrated in FIG. 2, the inferior vertebra 202 further includes a first pedicle 214, a second pedicle 228, a first lamina, and a second lamina. Further, a vertebral foramen 222 is established within the inferior vertebra 202. A spinal cord 216 passes through the vertebral foramen 222. Moreover, a first nerve root 218 and a second nerve root 226 extend from the spinal cord 216. In particular, the first pedicle 214 and the second pedicle 228 represent regions of the spine in which surgeons often choose to implant anchors, such as bone screws for attaching an anchor and rod system to the spine. Notably, given the proximity to the spinal cord 216 and other significant anatomical portions, the implantation of such screws is a delicate and precise procedure requiting tools significantly different than available to the general public.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2. The first and second cervical vertebrae are structurally different than the rest of the vertebrae in order to support a skull.

Figure 3:
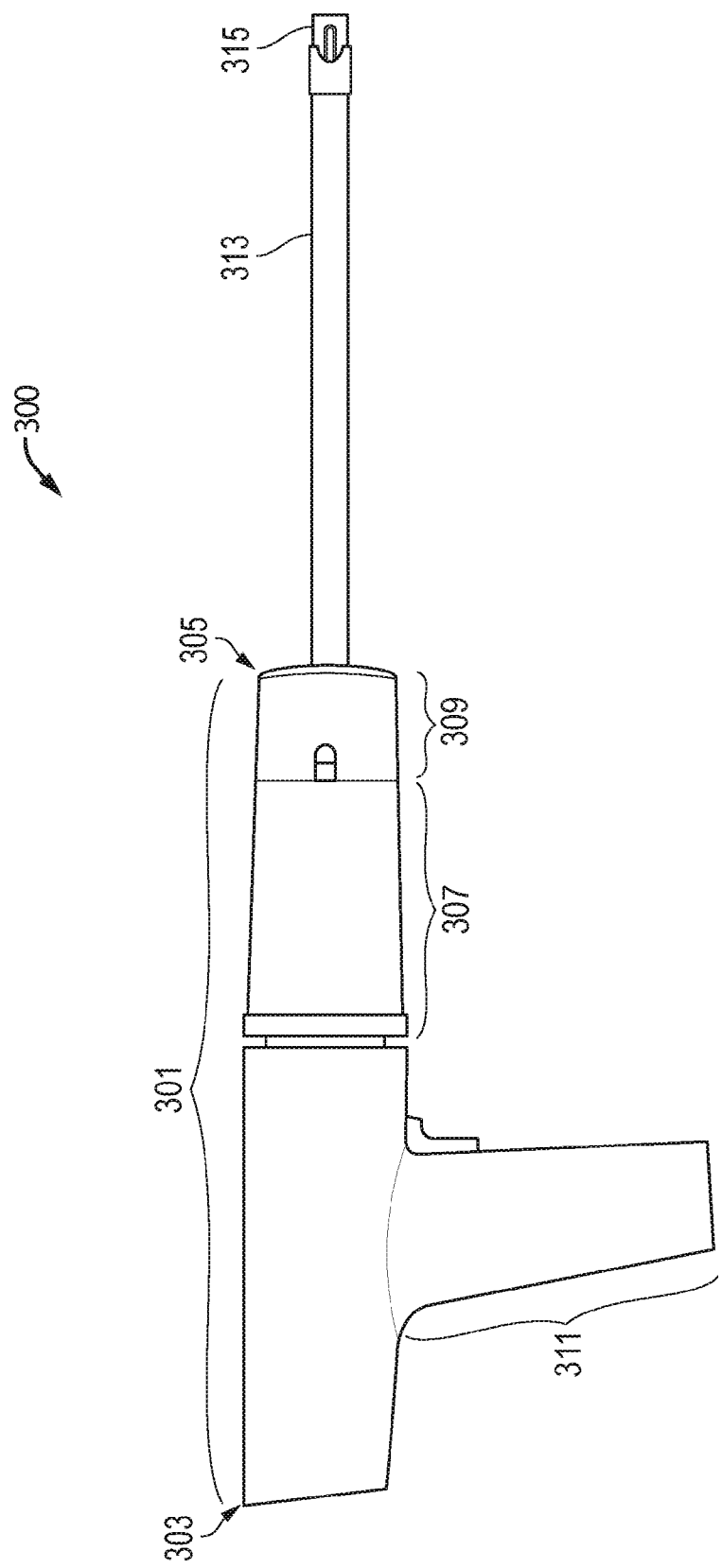
FIG. 3 includes a side view of a surgical tool in accordance with an embodiment.

Referring now to FIGS. 3-19 embodiments describing a surgical tool, its components and methods of using the surgical tool are provided. Accordingly, referring to FIG. 3 a side view illustration of a surgical tool is provided in accordance with an embodiment. As illustrated, a surgical tool 300 includes a housing 301 having a proximal end 303 and a distal end 305. The housing 301 further includes a handle portion 311 coupled to the housing 301 between the proximal end 303 and the distal end 305. As further illustrate, the surgical tool 300 includes a bayonet portion 309 coupled to the housing 301 adjacent to the distal end 305, and a sleeve portion 307 coupled to the housing 301 and abutting the bayonet portion 309. The surgical tool 300 further includes an effector, or in particular embodiments, an output shaft 315, coupled to the housing 301 adjacent to the distal end 305. The surgical tool 300 further includes a reaction arm, or in accordance with particular embodiments, a counter-torque sleeve 313, overlying the output shaft 315 and coupled to the housing 301 adjacent to the distal end 305.

Figure 4:
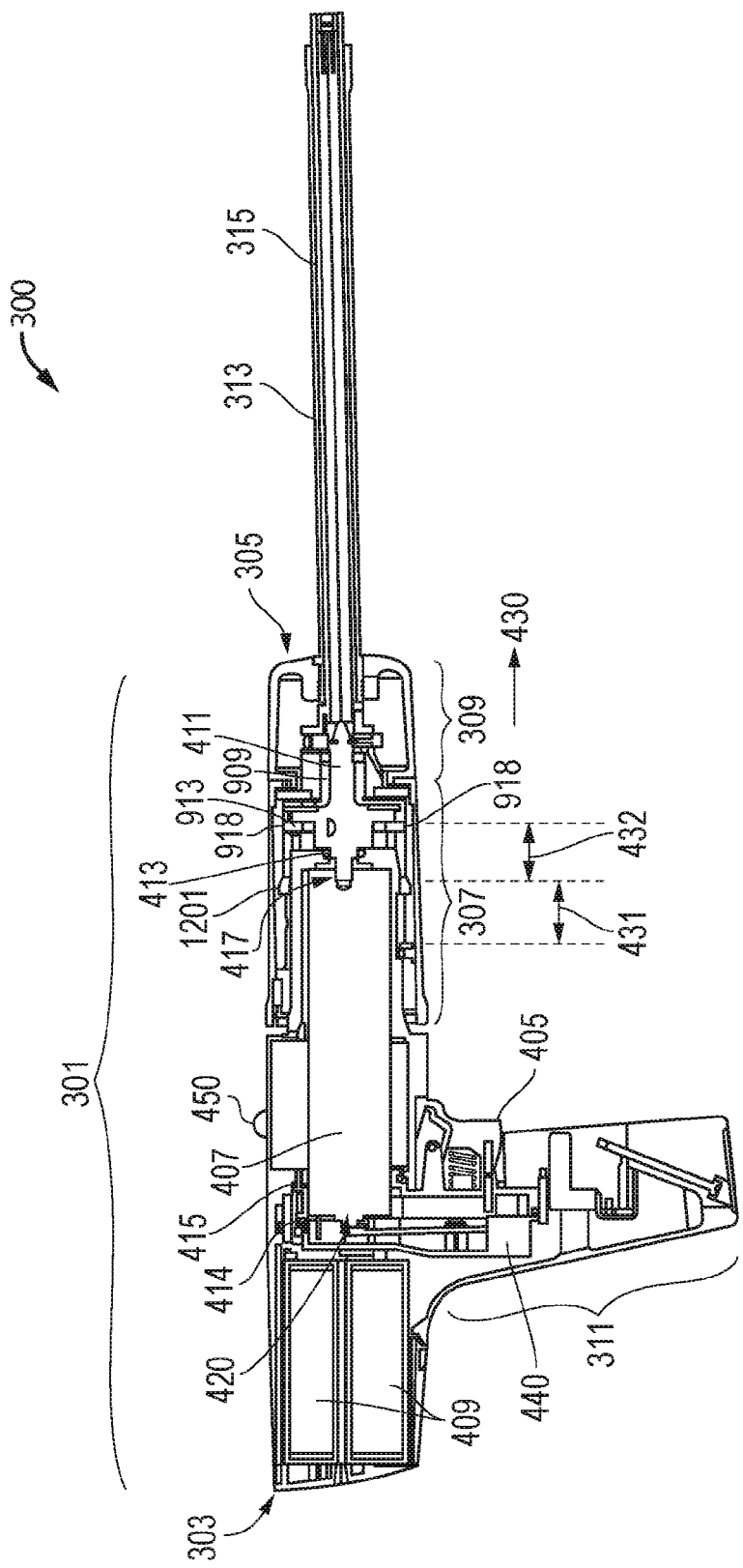
FIG. 4 includes a cross-sectional illustration of a surgical tool in accordance with an embodiment.

Referring to the surgical tool 300 with more particularity, FIG. 4 provides a cross-sectional illustration of the surgical tool in accordance with one embodiment. The cross-sectional illustration of FIG. 4 is provided for clarity and to illustrate the interaction of all the components, as such may be referred to throughout the detailed description.

In reference to the operation of the tool, generally the surgical tool 300 is capable of providing a rotational force to an implant via the output shaft 315. In particular, a user depresses a trigger 405 coupled to the handle 311 which is coupled to an actuator 440. The actuator 440 is coupled to a motor 407 and configured to engage the motor 407 such that a motor shaft 411 is rotated upon actuation of the motor 407. Depending upon the position of a sleeve portion 307 and components within the sleeve portion, which will be described in more detail herein, the motor shaft 411 can be coupled to the output shaft 315 which in turn will cause rotation of the output shaft 315. According to a particular embodiment, coupling of the motor shaft 411 and output shaft 315 is facilitated by axial movement of the sleeve portion 307 such that components within the sleeve including a spline drive 913 and hex drive output gear 909 are operably coupled and result in coupling of the motor shaft 411 and the output shaft 315. Moreover, axial movement of the sleeve portion 307 causes respective axial movement of the counter-torque sleeve 313 such that the counter-torque sleeve 313 can be positioned on the implant engaged by the output shaft 315.

In further reference to the general operation of the surgical tool 300, the motor 407 can be a DC electric motor and accordingly can be electrically connected to power sources 409, including for example batteries. According to one embodiment, the power sources 409 can be disposed in a housing, such as a battery pack, that is adjacent to the proximal end 303 of the housing 301.

The surgical tool 300 can further include optical indicator 450 coupled to the housing and configured to provide feedback to the user regarding a state of the tool. Generally, the optical indicator 450 can be electrically coupled to the power sources 409. In one embodiment, the optical indicator 450 can include a light, such as a light emitting diode (LED). In a more particular embodiment, the optical indicator 450 can indicate whether the sleeve portion 307 and the counter-torque sleeve 313 have traveled a requisite axial distance such that the tool will operate. Accordingly, in such embodiments, the light may further be electrically coupled to a switch or a microprocessor.

Additionally, the surgical tool 300 can further include an audible indicator coupled to the housing and configured to provide feedback to the user regarding a state of the tool. Accordingly, the audible indicator can provide the same function as the optical indicator as described above.

In reference to components at the distal end of the surgical tool 300, according to one embodiment, the output shaft 315 is coupled to the housing 301. According to a particular embodiment, the output shaft 315 is coupled to the motor shaft 411 which is directly connected to the motor 407 and the motor is directly connected to the housing 301. Moreover, the counter-torque sleeve 313 overlies the output shaft 315 and is coupled to the housing 301. In accordance with one particular embodiment, the counter-torque sleeve 313 is directly connected to the bayonet 309 that is a portion of the housing 301. As such, in accordance with an aspect of the present disclosure, the output shaft 315 and the counter-torque sleeve 313 are coupled to the housing such that upon rotation of the output shaft 315 on an implant the forces transmitted by the output shaft 315 and the counter-torque 313 are balanced by their respective couplings to the housing 301.

As the surgical tool 300 is intended for use in surgeries, the tool, and more particularly components contained therein, must be sterilizable. As such, in accordance with one particular embodiment, components of the surgical tool 300, including for example, the output shaft 315, the counter-torque sleeve 313, the bayonet portion 309, and portions of the housing 301 are made of materials that are autoclavable. As such, the components must be capable of withstanding temperatures in excess of 130° C., as well as pressures in excess of 140 psi. In one embodiment, components illustrated in FIG. 3 can be made of a metal or metal alloy. Suitable metal or metal alloys can include tungsten, magnesium, aluminum, iron, cobalt, nickel, titanium, steel, chromium, or any combinations thereof. In another embodiment, the components illustrated in FIG. 3 can include a non-metal, such as carbon, and more particularly carbon fiber. In accordance with another embodiment, the components within the surgical tool 300 can include high temperature polymer materials. In a more particular embodiment, suitable polymer materials can include polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof. Other suitable materials can include styrenes (e.g., acrylonitrile butadiene styrene), polycarbonates, and polysulphones.

Moreover, portions of the housing 301 can be sealed. In accordance with one particular embodiment, the motor 407 is within the sealed portion of the housing 301. In accordance with another embodiment, seals 413, 414, and 415, such as o-rings, which are provided to create a sealed portion around the motor 407 such that the surgical tool 300 can be sterilized without damaging the motor 407. In a more particular embodiment, a single o-ring 413 is provided between the distal end 417 of the motor 407 and the motor shaft 411, while a double o-ring seal provided by o-rings 414 and 415 are provided proximate to the proximal end 420 of the motor 407.

According to one particular embodiment, the torque provided by the output shaft to an implant can be limited, and more particularly selectable. According to one embodiment, the torque output by the tool can be limited by an electrical system wherein the current provided to the motor is controlled and may be selectable by the user. In such an embodiment, a microprocessor call be electrically coupled to the motor and battery to control the current to the motor. According to an alternative embodiment, a mechanical torque limiter can be coupled to the motor shaft to limit the torque. In one such embodiment, the torque limiter can include the use of bearings and a clutch which disengages an input shaft from an output shaft if a certain torque is exceeded.

Figure 5:
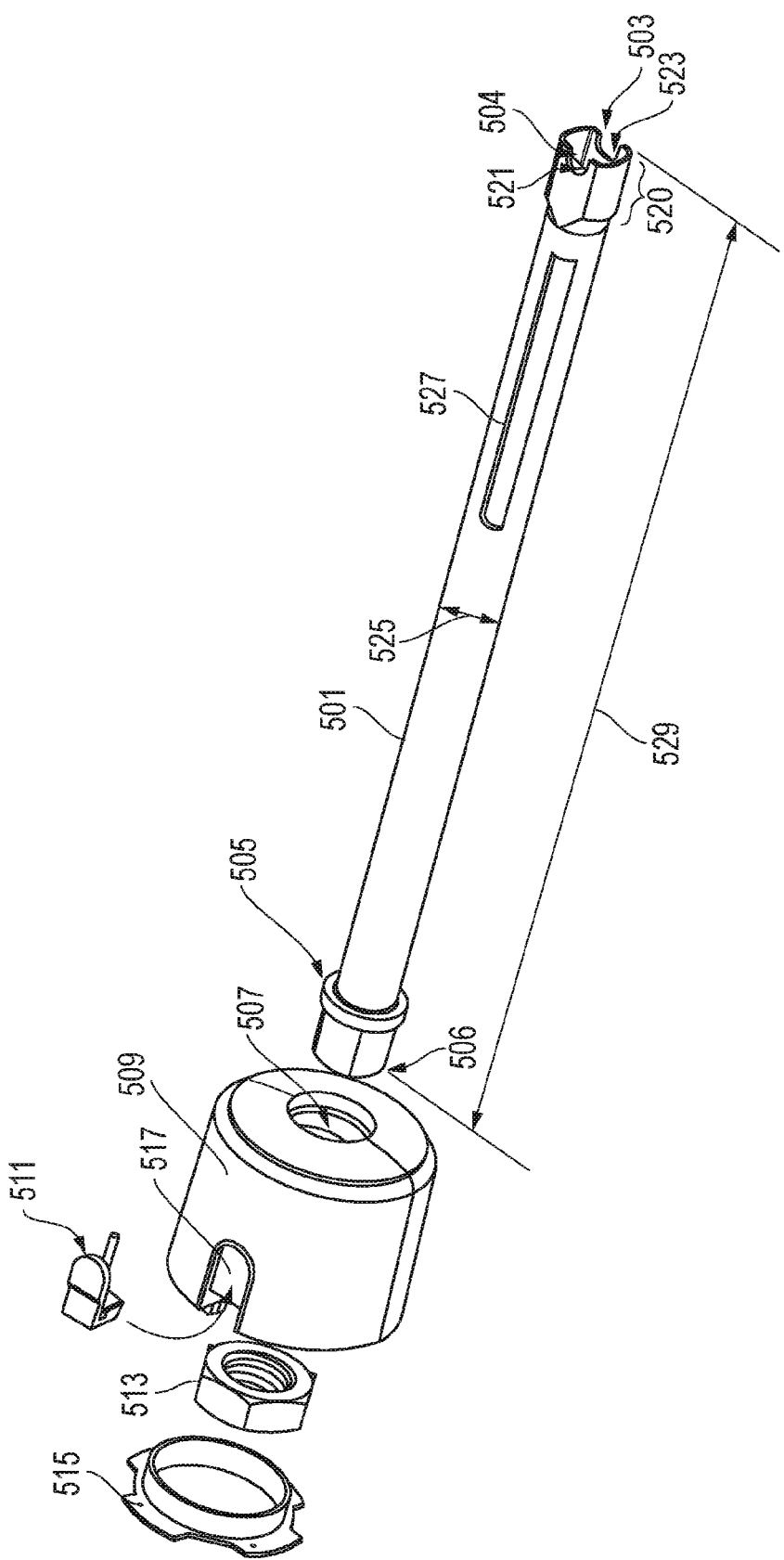
FIG. 5 includes a perspective view of the bayonet portion of the surgical tool in accordance with an embodiment.

Referring now to particular portions of the surgical tool 300, FIG. 5 includes a perspective view of a portion of the surgical tool including the counter-torque sleeve and the bayonet portion in accordance with an embodiment. Generally, the counter-torque sleeve 501 includes a proximal end 506 and a distal end 504. Moreover, the counter-torque sleeve 501 includes an opening 503 adjacent to the distal end 504 and configured to engage a portion of an implant. The counter-torque sleeve 501 can be coupled, more particularly directly connected to the bayonet portion 509 through the opening 507. In accordance with a particular embodiment, the counter-torque sleeve 501 is directly connected to the bayonet portion 509 such that the ring portion 505 adjacent to the proximal end 506 of the counter-torque sleeve 501 engages the inner surface of the bayonet portion 509 and fixable attaches the two components. Additionally, a nut 513 having threads along the inner surface can be coupled to the distal end 506 of the counter-torque sleeve 501 and directly connect the counter-torque sleeve 501 with the bayonet portion 509. Moreover, a lock ring 515 can be inserted within the bayonet portion 509 to facilitate coupling of the bayonet 509 and counter-torque sleeve 501 with the housing of the tool.

In accordance with one embodiment, the bayonet portion 509 can further include a decoupling structure to release the bayonet portion 509 from the housing of the tool. In one particular embodiment, the bayonet portion 509 includes a release tab 511 directly connected to the bayonet portion 509 and configured to be depressed and facilitate removal of the bayonet portion 509 from the housing.

As illustrated, the counter-torque sleeve 501 includes the opening 503 adjacent to the distal end 504 and configured to engage an implant. In accordance with one embodiment, the counter-torque sleeve 501 includes a head portion 520 shaped to include channels 521 and 523 that are configured to engage an implant. In a particular embodiment, the channels 521 and 523 are particularly designed to engage an implanted rod. In an alternative embodiment, the counter-torque sleeve 501 can include a pin extending from the head portion 520 configured to engage the implant and lock the position of the counter-torque sleeve 501 relative to the implant. In another particular embodiment, the head portion 520 can include more than one pin, such as two pins, that may be oriented on opposite sides of the head portion 520 and configured to engage the implant. Still, in accordance with another embodiment, the head portion 520 can be a conformable construct. For example, a conformable construction can include an array of pins disposed within the head portion 520, such that each of the pins are axially movable along the length of the counter-torque sleeve 501 and upon engagement with an implant, some of the pins are moved axially, while others are remain unmoved and couple with the engagement.

Generally, the counter-torque sleeve 501 can be freely rotatable around the longitudinal axis defined by the length. Rotational freedom facilitates initial engagement of the head portion 520 with an implant. In one embodiment, the counter-torque sleeve 501 is freely rotatable around the longitudinal axis by an angle of at least about 20°. In accordance with another embodiment, the angle of rotation can be greater, such as at least about 30°, at least about 45°, or even at least about 60°. In one particular embodiment, the counter-torque sleeve 501 is freely rotatable around the longitudinal axis by an angle of not greater than about 360°, not greater than about 180°, or even not greater than about 90° to facilitate engagement with the implant.

Generally, the counter-torque sleeve 501 has a length 529 defined between the proximal end 506 and the distal end 504 of at least about 15 cm. In accordance with another embodiment, the length 529 of the counter-torque sleeve 501 can be greater, such as at least about 18 cm, such as at least about 20 cm, or even at least about 22 cm. Still, however, in accordance with another embodiment, the length 529 of the counter-torque sleeve 501 is generally not greater than about 40 cm, such as not greater than about 30 cm, or even not greater than about 25 cm. In accordance with one particular embodiment, the counter-torque sleeve 501 has a length 529 within a range between about 20 cm and about 25 cm.

Additionally, the counter-torque sleeve 501 typically has a diameter 525 along its mid-length that is greater than a diameter of the output shaft such that the output shaft can extend through the interior of the counter-torque sleeve 501 and the counter-torque sleeve 501 can slidably engage the output shaft and portions of the implant. As such, in one particular embodiment, the counter-torque sleeve 501 has a diameter 525 of at least about 8 mm. In another embodiment, the diameter 525 is greater, such as at least about 9 mm, or even at least about 10 mm. In accordance with one particular embodiment, the diameter 525 of the counter-torque sleeve 501 is not greater than about 15 mm, such as not greater than about 12 mm. As such, in one more particular embodiment, the diameter 525 of the counter-torque sleeve 501 is within a range between about 10 mm and about 12 cm.

Still, it should be noted that while the illustrated embodiments describe the arrangement of the output shaft within the counter-torque sleeve 501, in certain alternative embodiments, the counter-torque sleeve 501 is located within the output shaft. In such embodiments the output shaft is external to the counter-torque sleeve 501, and the counter-torque sleeve 501 is disposed within the interior of the output shaft, and configured to engage portion of the implant. For example, in one particular embodiment, the implant can include a nut with a screw extending through it, wherein the counter-torque sleeve 501 is configured to engage the head of the screw, while the output shaft has a greater diameter, slideably engages over the counter-torque sleeve 501 and is configured to engage the nut. Accordingly, for such embodiments, the diameter of the counter-torque sleeve 501 can be less than described above.

In another embodiment, the counter-torque sleeve 501 can include a viewing port 527 along its length 529. In particular, the viewing port 527 can include an opening or transparent portion whereby the user can view the underlying output shaft contained within the interior of the counter-torque sleeve 501. More particularly, the viewing port 527 can be aligned with a similar structure (i.e., another viewing port) within the output shaft thereby allowing the user to view contents within the output shaft. In accordance with one particular embodiment, the tool can be used to sever break-off portions of set screws and, accordingly, the viewing port 527 allows the user to confirm separation of the break-off portion as well as identify the number of break-off portions contained within the output shaft.

Generally, the viewing port extends for a portion of the length of the counter-torque sleeve 501. In one embodiment, the viewing port extends for a length of at least about 10% of the total length 529 of the counter-torque sleeve. In another embodiment, the viewing port extends for a length of at least about 25%, such as at least about 50%, or at least 75% of the total length 529 of the counter-torque sleeve 501. In one particular embodiment, the viewing port 527 can extend for substantially the entire length 529 of the counter-torque sleeve 501.

Additionally, the viewing port 527, or alternatively a portion of the counter-torque sleeve 501 can include indicia suitable for counting the number of contents therein. In the particular context of head portions removed from set screws, assuming all of the head portions have an equal length, indicia can be provided along the length of the viewing port 527 or along the length of the counter-torque sleeve 501 that facilitate counting of the head portions contained within.

As will be described in later embodiments, the counter-torque sleeve 501 is capable of axially translating along the length 529. In particular, some axial translation of the counter-torque sleeve 501 is required for operation of the tool. The particulars of this configuration and operation will be described in later embodiments.

Figure 6:
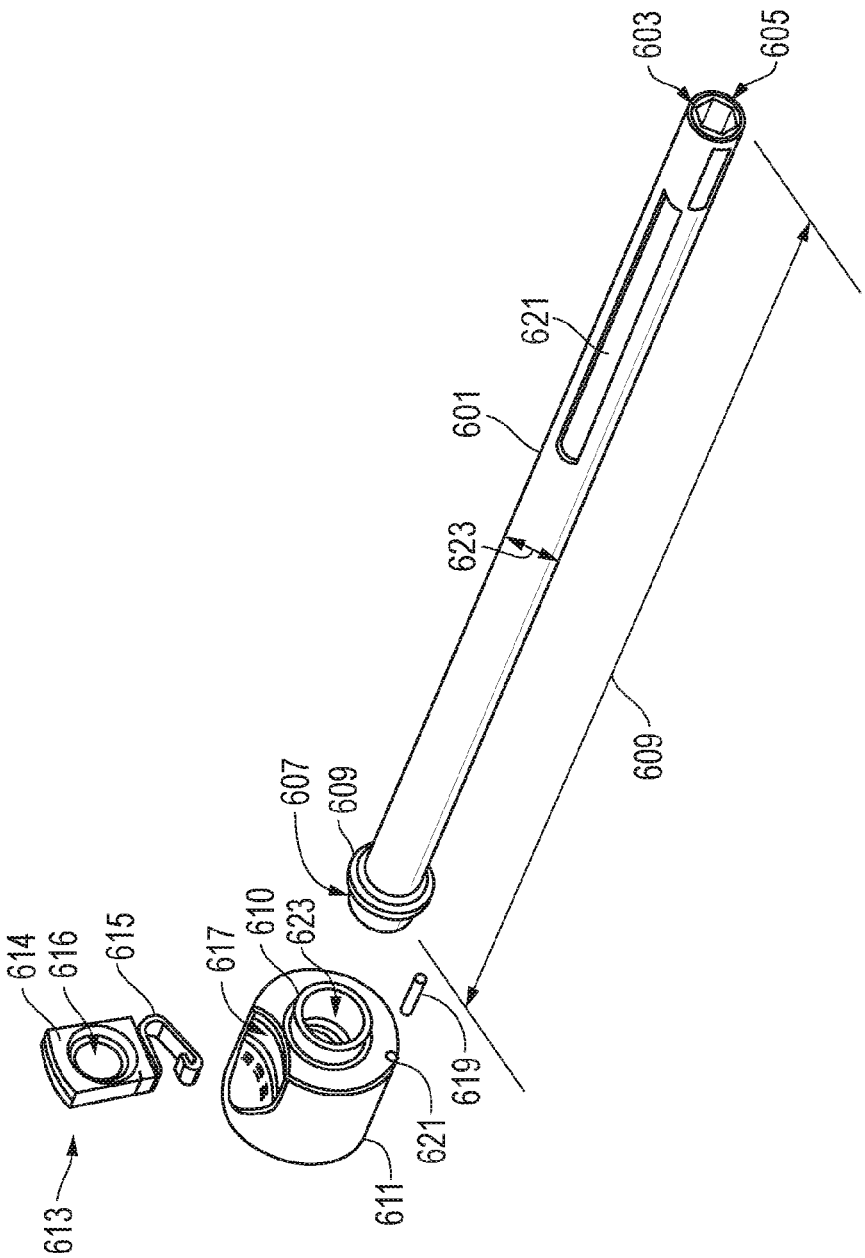
FIG. 6 includes a perspective view of a portion of the output shaft of the surgical tool in accordance with an embodiment.

FIG. 6 includes a perspective view of portions of the output shaft and inner coupler of the tool in accordance with an embodiment. As illustrated, FIG. 6 includes an output shaft 601, an inner coupling portion 611, and a coupler 613. As illustrated, the portion of the output shaft 601 adjacent to the proximal end 607 can slidably engage the interior surface of the collar 610 of the inner coupling portion 611. In particular, the inner coupling portion 6111 includes an opening 617 for receiving the coupling device 613. In particular, the coupling device 613 includes an upper portion 614 having an opening 616 and a biasing member 615 connected thereto. In accordance with a particular embodiment, the opening 616 is configured to engage the end of the motor shaft as will be illustrated in further embodiments. Moreover, a pin 619 is configured to the received within an opening 621 and engage the biasing member 615 of the coupling device 613 thereby operably connecting the coupler 613 and the inner coupling portion 611.

In particular reference to the output shaft 601, the output shaft 601 includes a proximal end 607 and a distal end 603 opposite the proximal end 607. Moreover, the output shaft 601 includes an opening 605 configured to engage an implant. In accordance with a particular embodiment, the opening 605 is configured to engage a head portion of a set screw, wherein the head portion is intended to be broken off or sheared from the bottom portion of the bone screw.

Generally, the output shaft 601 has a length 609 that is particularly designed to facilitate surgical procedures, notably a length suitable to minimize tool entrance into the body and avoid contamination of the surgical site while still having a suitable length for providing significant tactile feedback required for performing skilled surgical procedures. As such, in accordance with one embodiment, the output shaft 601 has a length 609 of at least about 10 cm. In one embodiment, the output shaft 601 has a length 609 of at least about 15 cm, such as at least about 18 cm, or even at least about 20 cm. In another embodiment, the length 609 of the output shaft 601 is not greater than about 40 cm. Still, the length 609 of the output shaft 601 may be further limited, such as not greater than about 35 cm, or not greater than about 30 cm. As such, in one particular embodiment, the output shaft 601 has a length 609 within a range between about 20 cm and about 30 cm. The output shaft 601 further includes a viewing, port 621 having the same characteristics as the viewing port described in accordance with FIG. 5.

Generally, the output shaft 601 has a diameter 623 measured along the mid-region between the proximal end 607 and the distal end 603 that is less than the diameter of the counter-torque sleeve. In one embodiment, the output shaft 601 has a diameter 623 of at least about 3 mm. In another embodiment, the diameter 623 is greater, such as at least about 4 mm, at least about 5 mm, or even at least about 6 mm. Typically, however, the diameter 623 of the output shaft 601 is limited such that it is not greater than about 12 mm. As such, in one particular embodiment, the output shaft 601 has a diameter 623 within a range between about 6 mm and about 10 mm.

As previously described, in some embodiments, the output shaft 601 can have a diameter that is greater than the diameter of the counter-torque sleeve, because in such embodiments the counter-torque sleeve is configured to be disposed within the output shaft 601. As such, in these embodiments, the diameter of the output shaft can be greater, such as greater than about 10 mm, greater than about 20 mm, or even greater than about 30 mm. Generally, in accordance with such embodiments, the diameter of the output shaft is within a range between about 10 mm and about 40 mm, and more particularly within a range between 10 mm and about 30 mm.

Figure 7:
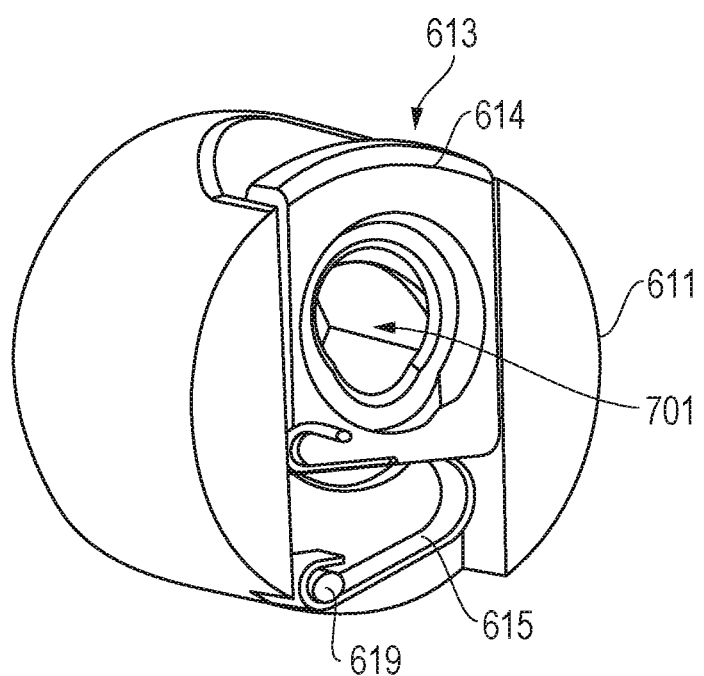
FIG. 7 includes a partial cross-section of a portion of the output shaft of the surgical tool in accordance with an embodiment.

Referring to FIG. 7, a partial cross-sectional illustration of the inner coupling portion 611 is illustrated for further clarity in accordance with an embodiment. As illustrated, the coupling device 613 is engaged within a slotted opening of the inner coupling portion 611. Generally, the pin 619 is configured to engage the biasing member 615 such that the coupler 613 is held within the coupling portion 611 until the user presses and releases the pin 619 from the biasing member. The coupler 613, and more particularly the opening 701, is designed to be of a size to prevent captured portions of an implant from falling into the tool during use or into the surgical field when the output shaft 601 is removed from the tool.

Figure 8:
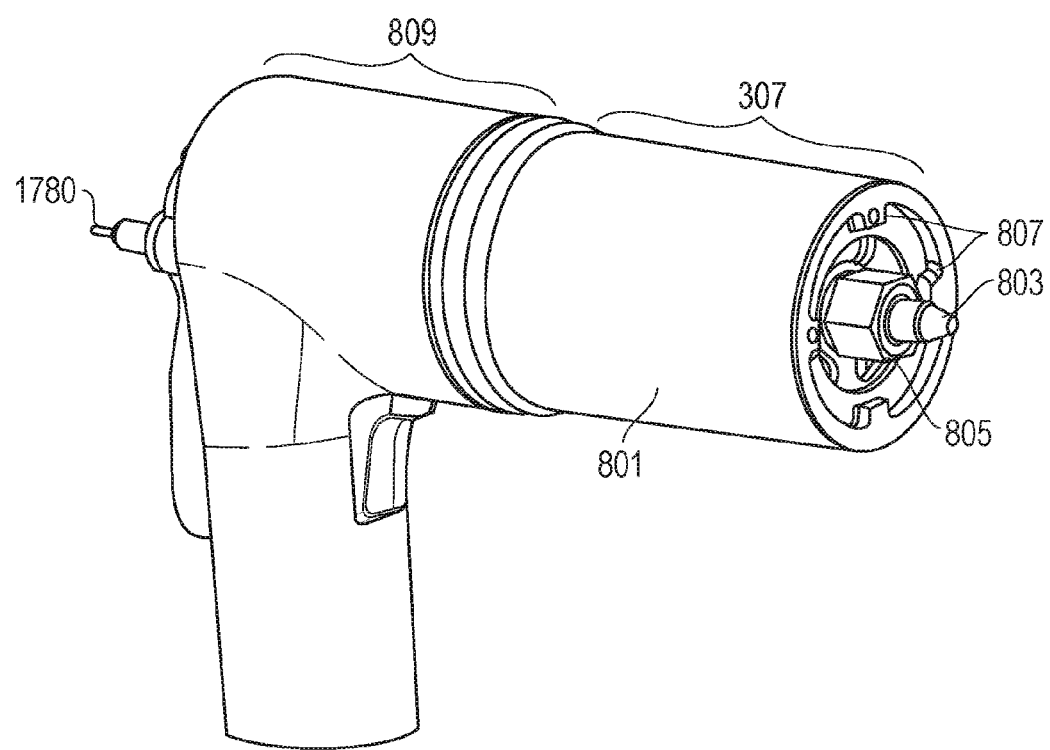
FIG. 8 includes a perspective view of a portion of the housing and sleeve of the surgical tool in accordance with an embodiment.

FIG. 8 includes a perspective of a portion of the surgical tool in accordance with an embodiment. FIG. 8 illustrates a portion of the housing 809 and more particularly the sleeve portion 307 previously illustrated in FIG. 3. The sleeve portion 307 includes an outer sleeve 801, which further includes flanges 807 configured to engaged the lock ring 515 of the bayonet portion 509 previously illustrated in FIG. 5. Moreover, FIG. 8 further illustrates a distal end of the motor shaft 803 extending from the sleeve portion 307. In accordance with one embodiment, it is this distal end of the motor shaft 803 which is configured to engage the opening 701 within the coupling device 613 and thus the inner coupling portion 611 previously illustrated in FIGS. 6 and 7.

Figure 9:
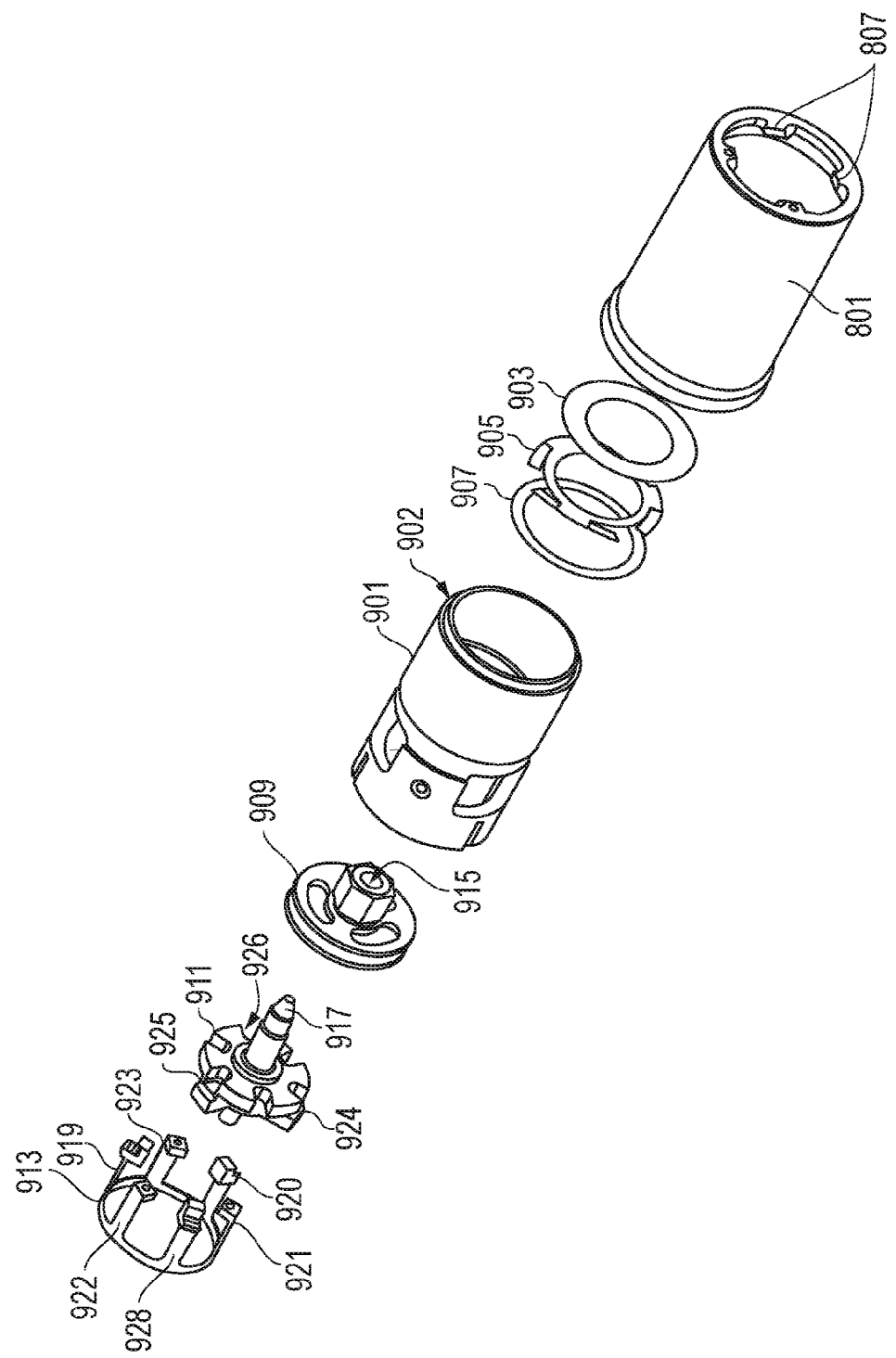
FIG. 9 includes an exploded view of components within a sleeve portion of the surgical tool in accordance with an embodiment.

Referring to FIG. 9, an exploded view of particular components within the sleeve portion of the surgical tool is illustrated in accordance with an embodiment. As illustrated, the outer sleeve portion 801 can include an inner sleeve portion 901 configured to slidably engage within the outer sleeve 801. Additionally, washers 903 and 907 can be disposed on either side of a biasing washer 905 and disposed within the outer sleeve 801. In particular, the washers 903 and 907 and the biasing washer can be disposed at the distal end of the outer sleeve adjacent the flanges 807 and biased against the lip 902 of the inner sleeve 901.

In accordance with a particular embodiment, the surgical tool includes a hex drive gear output 909 selectively coupleable to the motor shaft 911, which in turn is selectively coupleable to a spline driver 913. According to a particular embodiment, the hex drive output gear includes an opening 915 configured to receive the distal end 917 of the motor shaft 911. In accordance with a particular embodiment, the distal end 917 of the motor shaft 911 extends through the opening 915 of the hex drive output gear 909 and is configured to engage the coupling device 613 illustrated in FIG. 6. The spline driver 913 includes splines 918, 919, 920, 921, 922, and 923, (918-923) and in accordance with an embodiment, a portion of the splines 918-923 are configured to couple to portions of the motor shaft 911. In accordance with a particular embodiment, the splines 921, 922, and 923, are configured to fixably attach to portions 924, 925, and 926 of the motor shaft 911. According to another embodiment, the splines 918, 919, and 920, are not fixably coupled to the motor shaft and are, flexible portions which can flex radially inside the inner sleeve 901. Such a configuration facilitates selective coupling and decoupling of the motor shaft 911 from the output shaft by axial movement of the outer sleeve 801 and inner sleeve 901 relative to the remainder of the housing.

Figure 10:
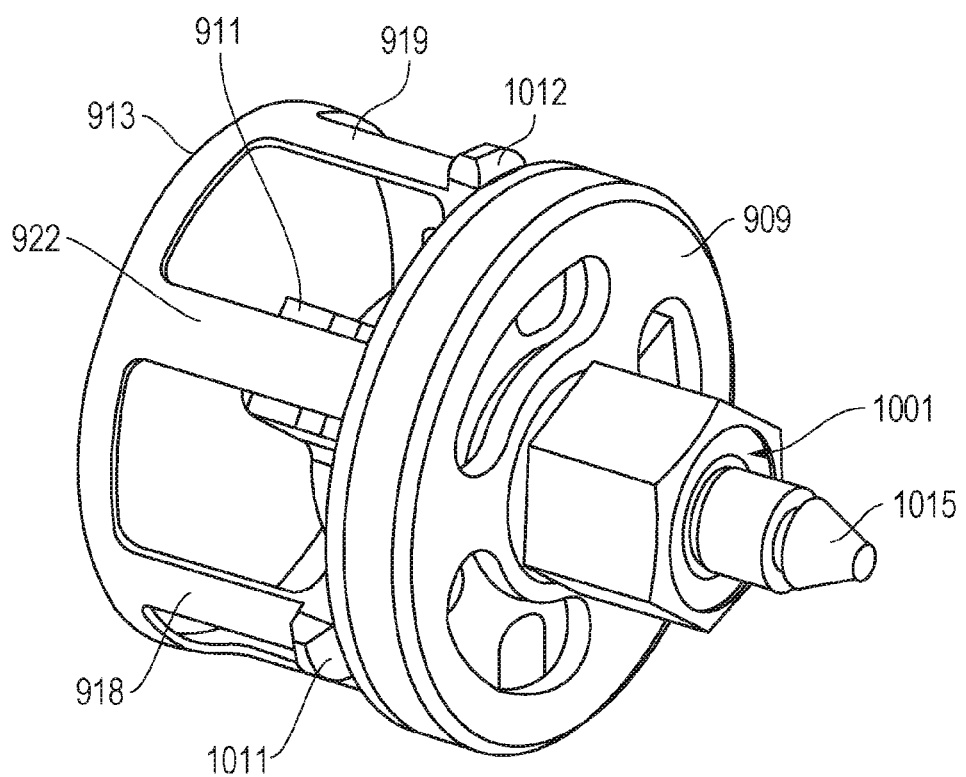
FIG. 10 includes a perspective view of components within the sleeve portion of the surgical tool in accordance with an embodiment.

Referring to FIG. 10, a perspective view of the spline driver, motor shaft, and hex drive output gear are illustrated in accordance with one embodiment. In particular, FIG. 10 illustrates the combination of the hex drive output gear 909 coupled with the motor shaft 911 and further coupled with the spline driver 913. As illustrated, the distal end 1015 of the motor shaft 911 extends through the opening 1001 of the hex drive output gear 909. In accordance with a particular embodiment, the spline driver 913 includes splines 918 and 919 that include portions 1011 and 1012 extending radially outward from the respective splines 918 and 919. The portions 1011 and 1012 are configured to engage a channel within the inner sleeve 901, allowing the splines 918 and 919 to radially expand and clutch portions of the hex drive output gear 909. The coupling of splines 918 and 919 with portions of the hex drive output gear 909 facilitates coupling the motor shaft 911 with the hex drive output gear 909 and as a result coupling the motor shaft 911 with the output shaft.

Figure 11:
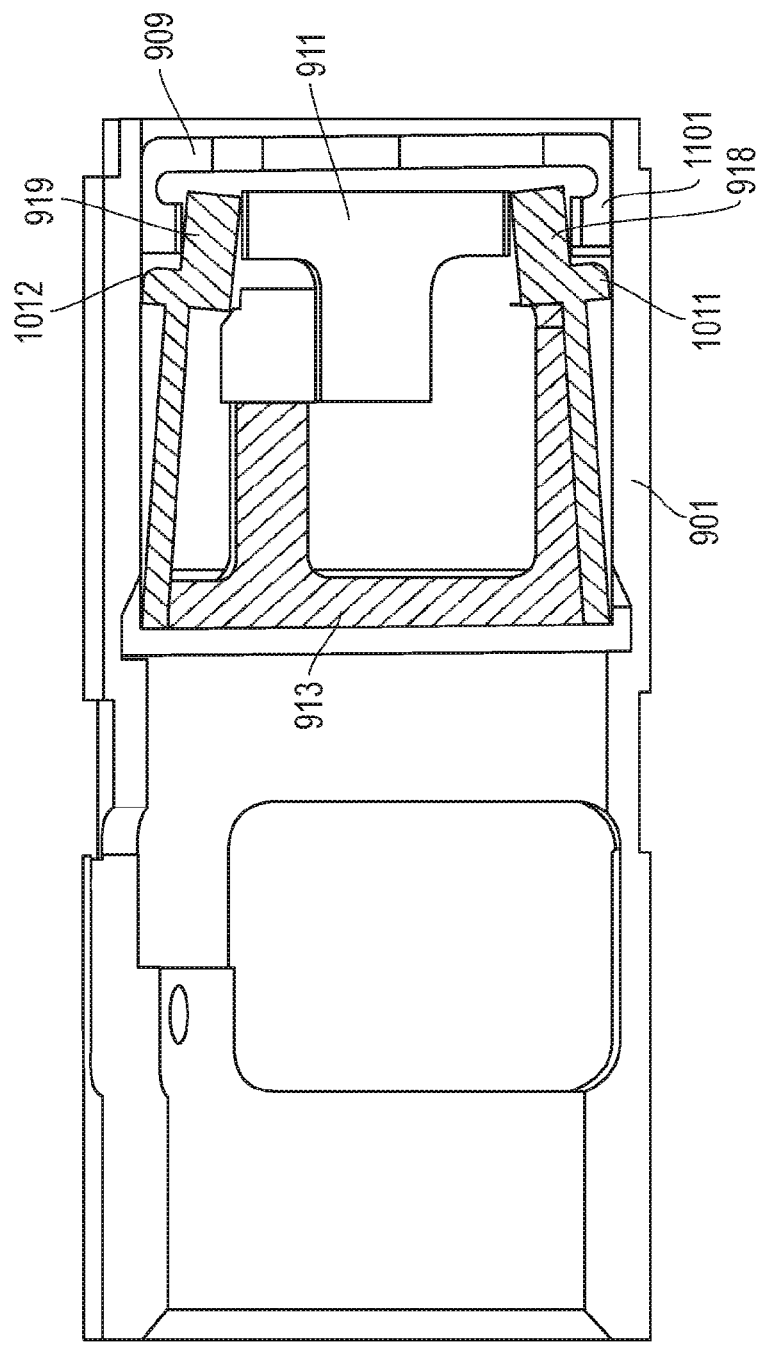
FIG. 11 includes a cross-sectional view of components within the sleeve portion of the surgical tool in accordance with an embodiment.
Figure 12:
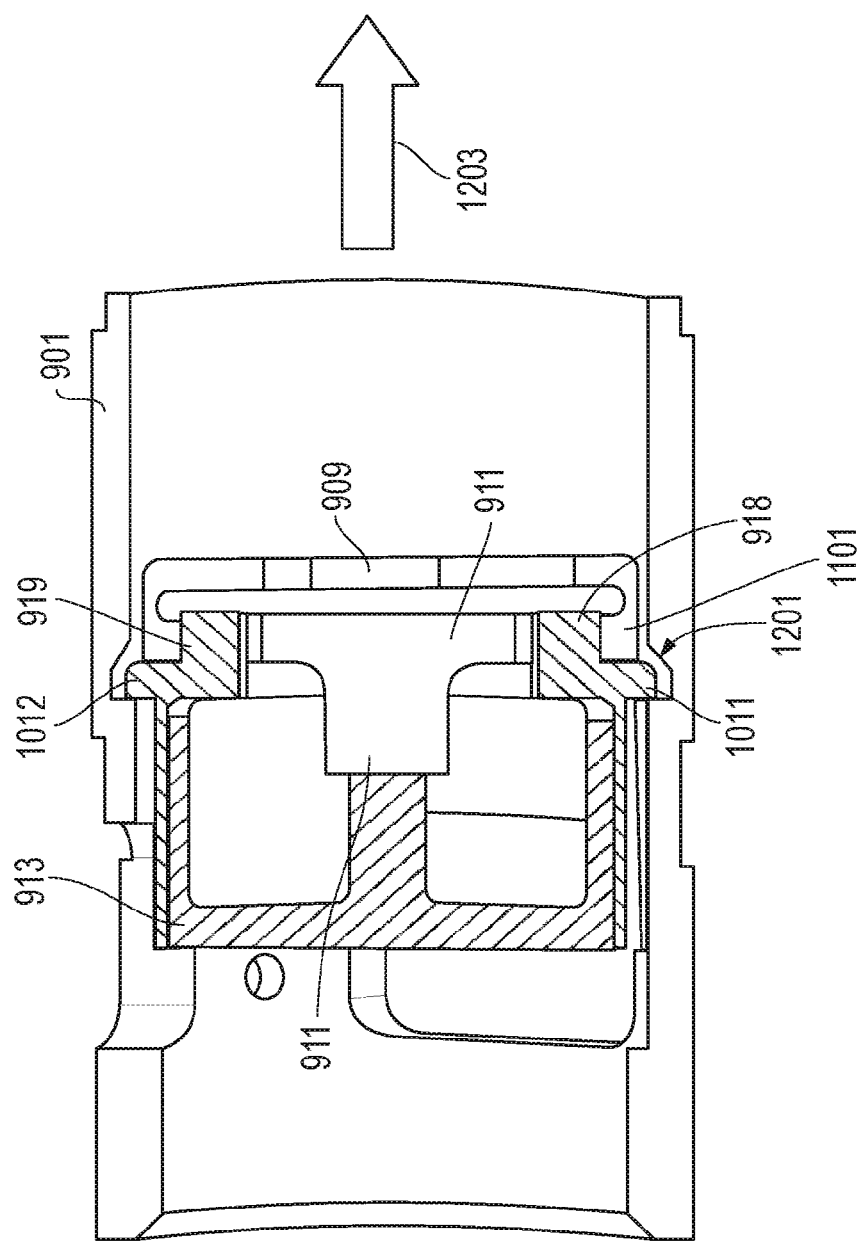
FIG. 12 includes a partial cross-sectional view of components within the sleeve portion of the surgical tool in accordance with an embodiment.

FIGS. 11 and 12 more clearly illustrate the clutching interaction between the spline driver and the hex drive output gear. Referring to FIG. 11, a partial cross-sectional illustration of the spline driver 913, motor shaft 911, and hex drive output gear 909 within the inner sleeve 901 is illustrated. In particular, as illustrated, the spline drive 913 is contained within the inner sleeve portion 901 such that the splines 918 and 919 are radially compressed. According to one particular embodiment, portions 1011 and 1012 engage the side walls of the inner sleeve portion 901 and radially compress the spline portions 918 and 919 thereby decoupling spline portions 918 and 919 from the lip portion 1101 of the hex drive output gear 909.

Referring now to FIG. 12, a partial cross-sectional illustration of portions of components including the spline driver 913, motor shaft 911, and hex drive output gear 909 are illustrated within the inner sleeve portion. Notably, the inner sleeve portion 901 has been moved forward axially in the direction 1203 with respect to the spline driver 913, motor shaft 911, and hex drive output gear 909. Accordingly, in moving the inner sleeve portion 901 forward axially, the splines 918 and 919, and more particularly the portions 1011 and 1012 of the splines 918 and 919 engage a channel 1201 within the inner surface of the inner sleeve portion 901. The engagement of portions 1011 and 1012 within the channel 1201 facilitate outward radial movement of the splines 918 and 919 and coupling of the splines 918 and 919 with the lip portion 1101 of the hex drive output gear 909. The engagement of the splines 918 and 919 with the hex drive output gear 909 facilitates coupling of the motor shaft 911 with the hex drive output gear 909 which in turn facilitates coupling of the motor shaft 911 with the output shaft of the surgical tool. Accordingly, selective coupling and decoupling of the motor shaft 911 with the output shaft is facilitated by axial movement of the inner sleeve portion 901 from a first position to a second position as illustrated in FIGS. 11 and 12 respectively.

Referring briefly again to FIG. 4, coupling of the motor shaft 411 to the output shaft 315 can be accomplished by axial movement of the sleeve portion 307 in the direction 430. In particular, for torque to be applied to the implant, some axial movement of the sleeve portion 307 is completed to couple the motor shaft 411 and the output shaft 315. Such a mechanism ensures that torque cannot be applied to the implant without sufficient engagement of the counter-torque sleeve 313 with the implant, thus avoiding potential for injury to the patient or the surgeon. According to a particular embodiment, the entire allowable movement of the sleeve portion 307, the bayonet portion 309, and the counter-torque sleeve 313 in the axial direction 430 is the axial travel distance 431. In accordance with a particular embodiment, the axial travel distance 431 is generally at least about 10 millimeters, such as at least about 20 millimeters, such as at least about 25 millimeters. In another embodiment, the axial travel distance 431 is limited such that it is not greater than about 50 millimeters, such as not greater than about 40 millimeters. As such, in one particular embodiment, the axial travel distance 431 is within a range between about 15 millimeters and about 30 millimeters.

More particularly, there is a distance 432 that is a fraction of the axial travel distance 431 that is sufficient to selectively couple the splines 918 and 919 within the channel 1201 and thereby couple the motor shaft 411 and output shaft 315. According to one embodiment, the distance 432 is not greater than about 95% of the axial travel distance 431. In another embodiment, the distance 432 is not greater than about 90% or even not greater than about 80% of the axial travel distance 431. Still, in another particular embodiment, the distance 432 sufficient to engage the splines 918 and 919 within the channel 1201 is at least about 50% of the total axial travel distance 431. The differences between the distance 432 and the axial travel distance 431 facilitates partial engagement of the counter-torque sleeve 313 with an implant without requiring the sleeve portion 307 and subsequently the counter-torque sleeve 313 to travel the entire axial travel distance 431 before engagement of the motor shaft 411 with the output shaft 315. Thus, the counter-torque sleeve 313 may not need to extend the entire axial travel distance 431 before the operator can apply rotational force to the implant via the output shaft 315. This may be particularly suitable in the context of performing surgeries where space is limited and full contact with an implant may not be possible.

Figure 13:
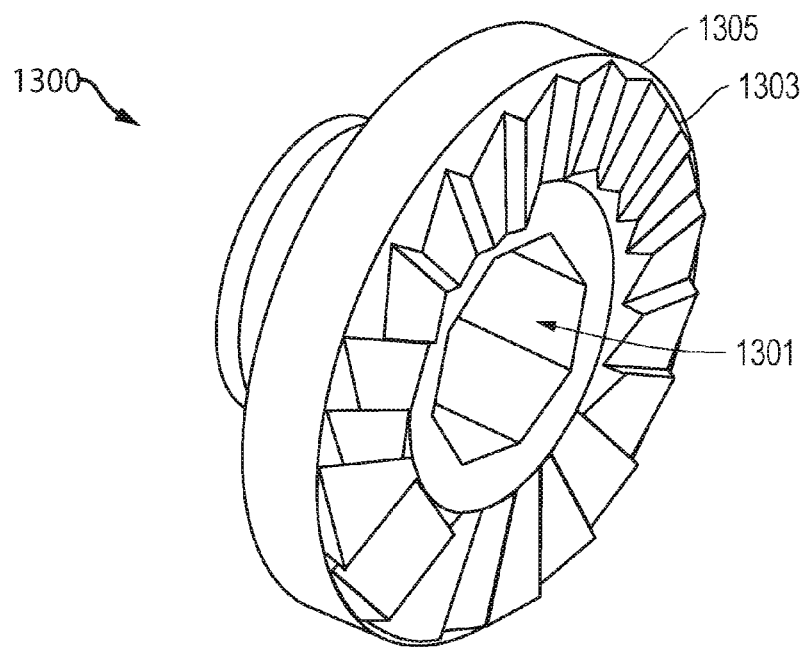
FIGS. 13 and 14 include clutch plates for use in a portion of the surgical tool in accordance with an embodiment.
Figure 14:
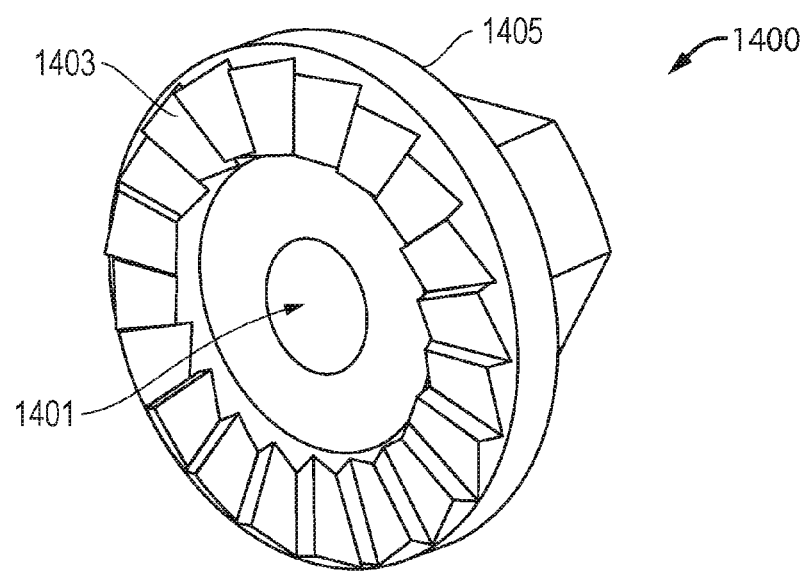

While embodiments herein have demonstrated a selective coupling between the motor shaft and the output shaft using a clutching mechanism having radial splines, it will be appreciated that other mechanisms are possible. For example, turning to FIGS. 13 and 14, alternative clutching mechanisms are illustrated suitable for coupling and decoupling the motor shaft and the output shaft. As illustrated, FIG. 13 includes a face clutch having an opening 1301 configured to couple with a portion of the motor shaft. Additionally, the face clutch includes a series of teeth 1303 disposed along a surface 1305 configured to engage teeth of a corresponding face clutch illustrated in FIG. 14. Accordingly, as illustrated in FIG. 14, the face clutch 1400 includes an opening 1401 configured to engage a portion of the motor shaft, as well as teeth 1403 disposed along the surface 1405 configured to engage the teeth 1303 of the corresponding face clutch 1300. Like the clutching mechanism utilizing the spline driver described previously, the face clutch mechanisms illustrated in FIGS. 13 and 14 are axially displaced until movement of the sleeve portion is sufficient for the faces to engage wherein the teeth of each surface engage each other and the motor shaft is coupled with the output shaft.

While particular embodiments herein have described mechanical means to selectively couple and decouple the motor shaft from the output shaft, it will be appreciated that electronic devices can be used. For example, in one embodiment, an electronic switch can be used to electrically disengage the motor from the battery until the sleeve portion travels a sufficient distance. As such, according to one embodiment before the sleeve portion is moved in an axial direction, the motor is electrically disengaged from the power source. After movement of the sleeve portion a sufficient axial distance, an electronic switch can be engaged or disengaged such that the motor is electrically coupled to the power source thereby allowing the motor shaft to turn the output shaft. Accordingly, in such embodiments using an electronic device for selective coupling and decoupling, the output shaft and motor shaft may be permanently connected.

Figure 15:
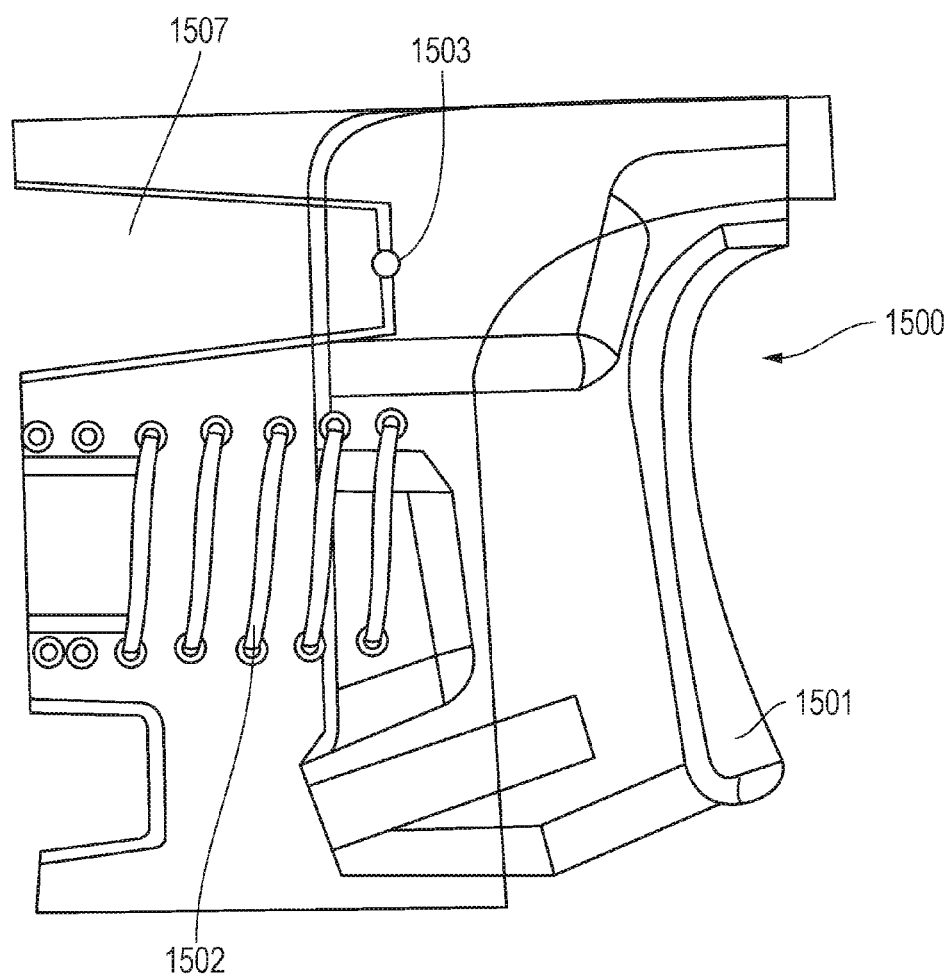
FIG. 15 includes a cross-sectional illustration of a trigger for use with the surgical tool in accordance with an embodiment.

Referring to FIG. 15, a cross-sectional illustration of a trigger in accordance with one embodiment is provided. As illustrated, a trigger 1500 is provided that includes a moveable trigger portion 1501 biased against a base portion 1507 by a biasing member 1502. As illustrated, the moveable trigger portion 1501 and base portion 1507 are pivotally connected at a pivot point 1503, such that the base portion 1507 can be fixably attached to the housing of the handle and the moveable trigger portion 1501 can pivot around the pivot point 1503 upon actuation by a user. In accordance with another embodiment, the trigger 1500 can include a magnetic trigger, including magnetic components, such as a reed switch.

Figure 16:
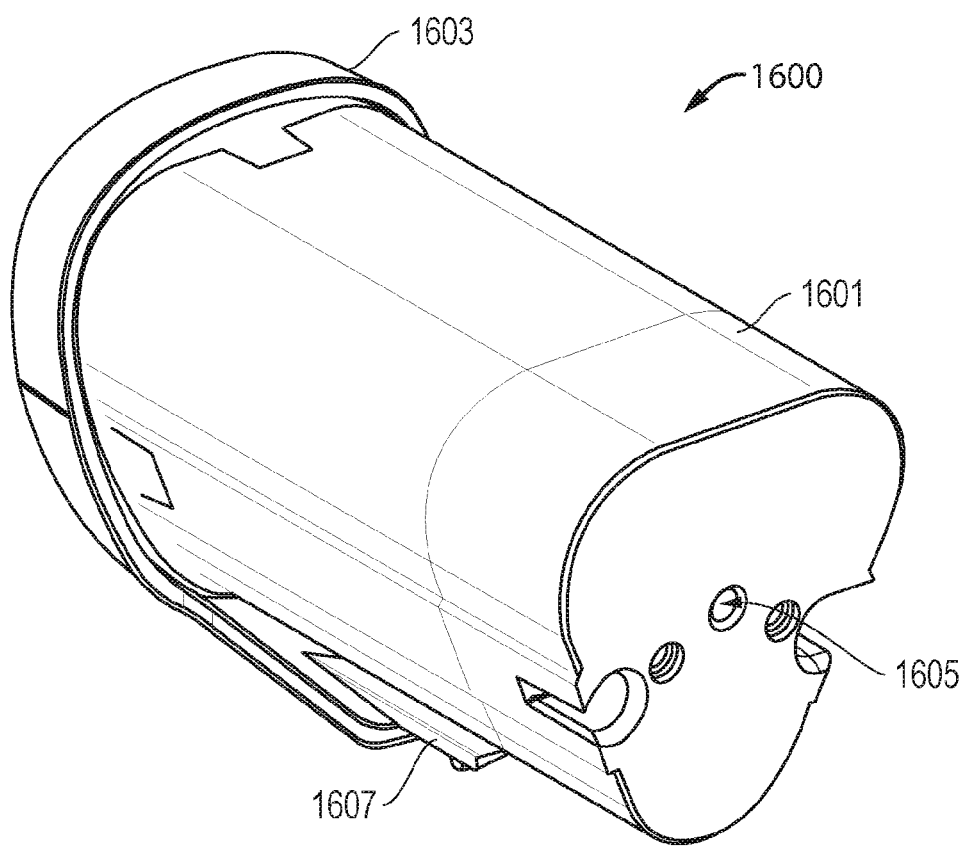
FIG. 16 includes a perspective view of a battery pack for use with the surgical tool in accordance with an embodiment.
Figure 17A:
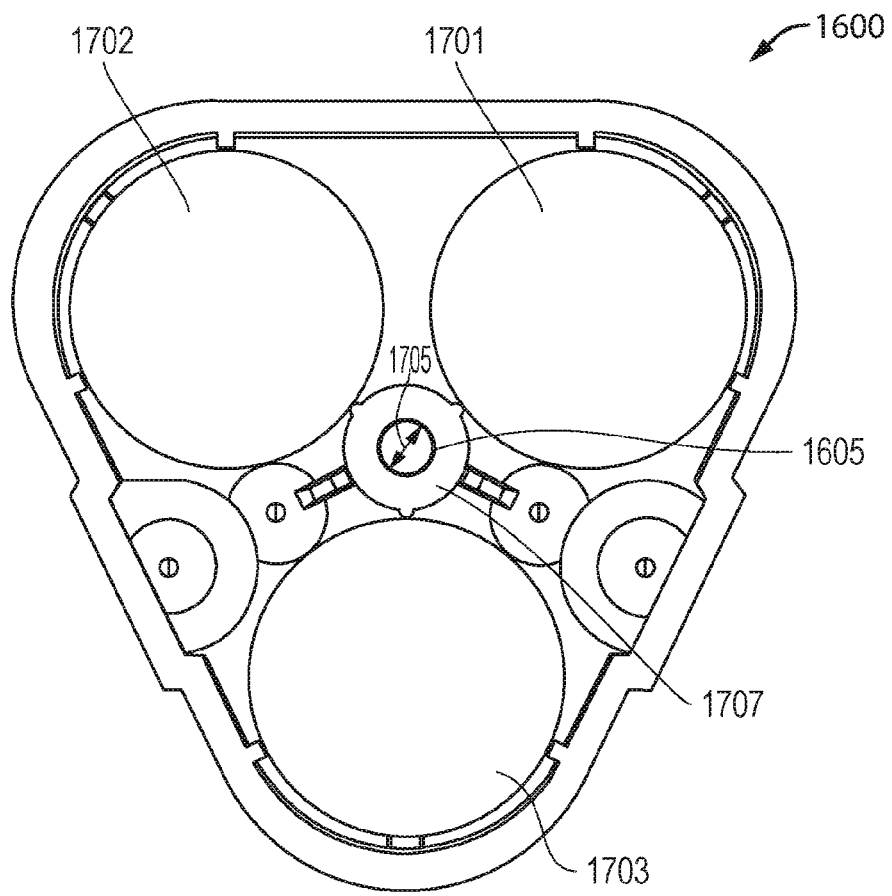
FIG. 17A includes a cross-sectional illustration of the battery pack for use with a surgical tool in accordance with an embodiment.
Figure 17B:
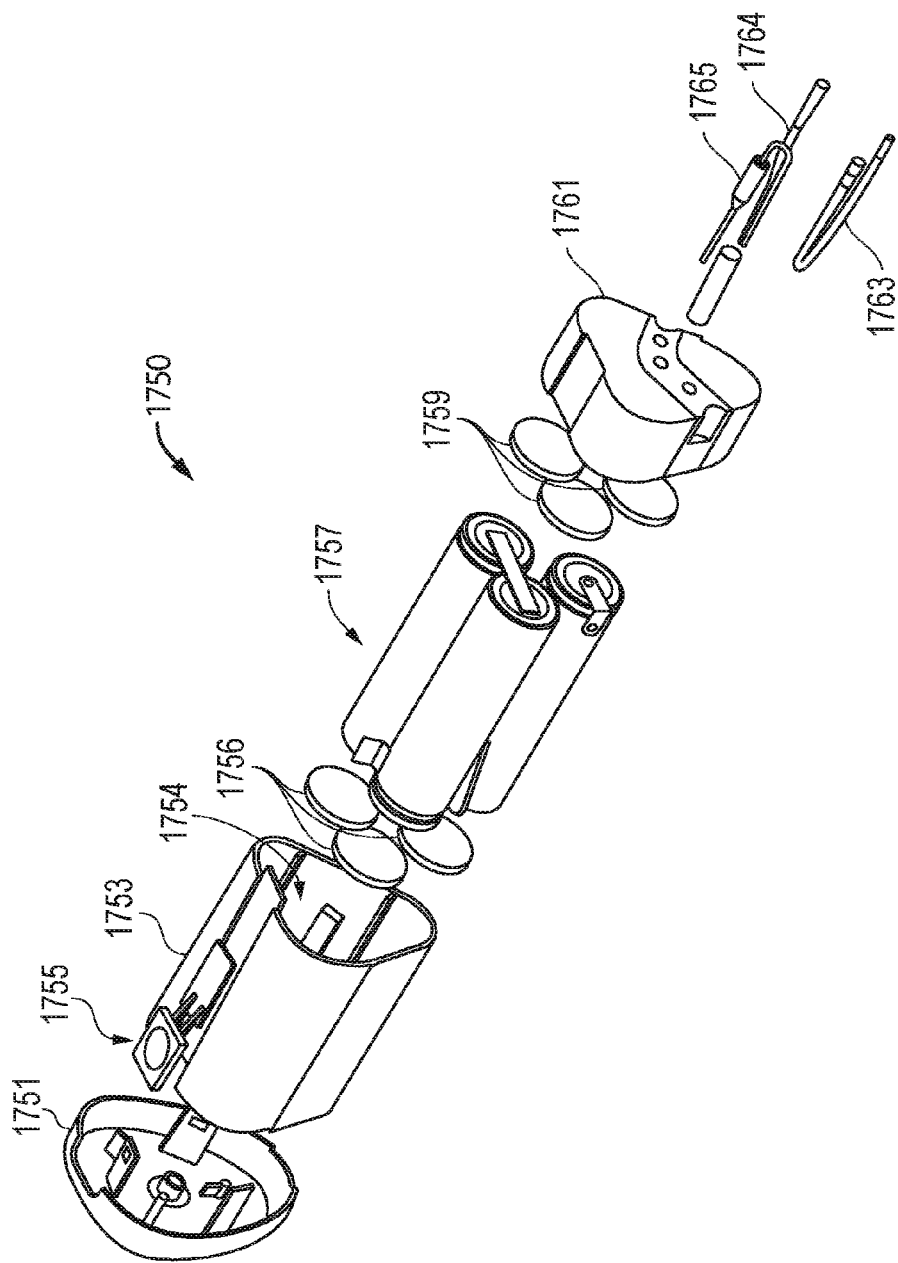
FIG. 17B includes a perspective view of another battery pack for use with a surgical tool in accordance with an embodiment.

FIGS. 16, 17A, and 17B illustrate particular embodiments of the battery pack. Referring to FIG. 16, a perspective view of a battery pack is illustrated in accordance with one embodiment. As illustrated, the battery pack 1600 includes a housing 1601 for containing the battery or batteries, and a cap portion 1603 coupled at one end of the housing 1601. According to a particular embodiment, the battery pack 1600 further includes a clip 1607 to fixably engage the battery pack 1600 within the housing. Moreover, in accordance with another embodiment, the battery pack 1600 includes a passage 1605 extending through the length of the battery pack 1600.

Referring to FIG. 17A, a cross-sectional illustration of a portion of the battery pack is illustrated in accordance with one embodiment. According to one embodiment, the battery pack 1600 has a generally triangular shape having generally three corners, wherein batteries 1701, 1702, and 1703 can be disposed within the three corners of the battery pack 1600. Moreover, in one embodiment, the passage 1605 extends along the longitudinal axis of the battery pack 1600 and between the batteries 1701-1703 such that the batteries 1701-1703 are arranged around the passage 1605. While the embodiment of FIG. 17A illustrated a battery pack 1600 having multiple battery cells 1701-1703, in accordance with another embodiment, the battery pack 1600 can include a single battery cell, such that the interior of the battery pack is one single power cell. In particular, with regard to embodiments using one battery, a passage may still be provided through the battery.

According to one embodiment, the passage 1605 has a diameter 1705 of at least about 1 mm. In another embodiment, the diameter 1705 of the passage 1605 is greater, such as at least about 1.5 mm or at least about 2 mm. In another embodiment, the passage 1605 has a diameter 1705 that is not greater than about 10 mm, such as not greater than about 8 mm, or not greater than about 5 mm. In one particular embodiment, the passage 1605 has a diameter 1705 within a range between 2 mm and about 5 mm.

In accordance with another embodiment, the passage 1605 has an electrically insulating sheath 1707. The electrically insulating sheath 1707 can include a dielectric material. According to one embodiment, suitable dielectric materials can include ceramics or polymers. In a more particular embodiment, the electrically insulating sheath 1707 includes a polymer. In accordance with another embodiment, the electrically insulating sheath can be made of a polymer material, including for example, polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof.

FIG. 17B includes a perspective view of another battery pack in accordance with an embodiment. As illustrated, the battery pack 1750 can include a rear cap 1751 coupled to a housing 1753, which can be further coupled to a front cap 1761. The rear cap 1751 can be coupled to the housing 1753 via a snap-fit connection, interference fit connection, or can include fasteners. Likewise, the front cap 1761 can be coupled to the housing 1753 via a snap-fit connection, interference fit connection, or through the use of fasteners.

The housing 1753 can include an engagement structure 1755 disposed on an upper surface and coupled to the body of the housing 1753. The engagement structure 1755 can be a user-operable device for releasing the battery pack 1750 front the housing 301 of the tool 300. According to one design, the engagement structure 1755 can be a cantilevered structure that is connected to the housing 1753 at one end and unsupported at the opposite end, facilitating depression of the unsupported end of the engagement structure 1755 toward the housing for release of the battery pack 1750 from the housing.

The housing 1753 can include a central opening 1754 extending longitudinally along the length of the housing 1753 for containing the power cells 1757 (i.e., batteries) therein. Additionally, the housing 1753 can include pads 1756 and 1759 corresponding to the each of the power cells 1757 and configured to suitable locate and secure the power cells 1757 within the housing 1753.

The battery pack of FIG. 17B includes three power cells 1757. The power cells 1757 may also be in a stacked orientation along the longitudinal axis with a first power cell 1757 aligned with and stacked at an end of a second power cell 1757. In one embodiment, the battery pack includes a total of nine power cells 1757 with three levels each having three power cells 1757. These stacked power cells 1757 form a cross-sectional triangular arrangement similar to the arrangement of FIG. 17B. In one specific embodiment, the power cells are 1.2 V nickel-cadmium cells.

According to one embodiment, the battery pack 1750 can further include charging members 1763 and 1764. The charging members 1763 and 1764 can provide a suitable electrical connection between the power cells 1757 and an external power source for charging and/or recharging of the power cells 1757. The charging members 1763 and 1764 can be positioned within a portion of the housing 1753 and a portion of the front cap 1761. In particular designs, at least a portion of the charging members 1763 and 1764, such as an electrical contact portion is accessible from an opening within the front cap 1761. In such embodiments, the battery pack 1750 can be removed from the tool and engaged with an external power source via the electrical contact portion of the charging members 1763 and 1764 to recharge the power cells 1757.

In accordance with one particular embodiment, the tool can be used without the battery pack 1750 and incorporate a direct connection via an electrical cable to a remote power source via electrical contact 1780 illustrated in FIG. 8. This design facilitates use of the tool with an alternative power source. For example, if the power cells 1757 are drained or fail, the tool 300 can be directly connected to an external power source for operation of the tool 300. Operation of the tool from the battery pack 1750 or an external power source provides a failsafe operation mode if one particular power source of the tool is unavailable or fails.

The battery pack 1750 can further include a failsafe switch 1765 that is electrically coupled to the power cells 1757. The failsafe switch 1765 is operable between an on state and an off state. In the on state, the failsafe switch 1765 can allow current to flow between the power cells 1757 and the motor 407 within the tool 300. In the off state, the failsafe switch interrupts current flow between the power cells 1757 and the motor 407 to avoid inadvertent motor 407 operation during an off state condition of the failsafe switch 1765.

In certain designs, the failsafe switch 1765 can include a switch that is sensitive to a threshold temperature, such that the failsafe switch 1765 can be a thermal cutoff. For example, the failsafe switch 1765 can be in an on state until the battery pack 1750, and thus the failsafe switch 1765, is exposed to a temperature exceeding (i.e., either greater than or less than) a particular threshold temperature, in which case, the failsafe switch 1765 changes conditions to an off state. According to one particular embodiment, the failsafe switch 1765 can operate in an on state (i.e., allowing current flow) until the temperature of the battery pack 1750 is greater than a threshold temperature and then turns to an off state interrupting current flow to the motor 407, and otherwise electrically decoupling the power cells 1757 from the motor 407.

For one certain failsafe switch 1765, the threshold temperature can be a temperature of at least about 65° C., such as on the order of at least about 68° C., at least about 70° C., at least about 84° C., and particularly within a range between about 68° C. and about 84° C.

Certain designs of the failsafe switch 1765 can use a thermal fuse, in which after the threshold temperature is exceeded the electrical connection between the power cells 1757 and the motor 407 is permanently disconnected. In such designs, after the failsafe switch 1765 is changed to an off state, the battery pack 1750 will need to be removed from the tool and a new failsafe switch 1765 (i.e., thermal fuse) installed.

In other designs, the failsafe switch 1765 can be a thermal switch or thermal reset that can be made of a bimetallic material, in which after the threshold temperature is exceeded the electrical connection between the power cells 1757 and the motor is temporarily severed. The electrical connection can be reset after the temperature within the battery pack 1750 falls below the threshold temperature. In such embodiments using a thermal switch as the failsafe switch 1765, a user operable switch can also be integrated such that reset operation is not conducted without user operation. That is, when the electrical connection is temporarily disconnected between the power cells 1757 and the motor 407 by the failsafe switch, a user must operate a secondary failsafe switch or reset switch to reset the failsafe switch 1765 to an on state and reestablish an electrical connection between the power cells 1757 and the motor 407.

According to one embodiment, the failsafe switch 1765 can be operated at a range of voltages from about 9 V to about 11 V at 25° C., and more particularly over a range of voltages between about 9.5 V and about 10.1 V at 25° C. The failsafe switch 1765 can be operated at a current range of about 0-30 A.

Figure 35:
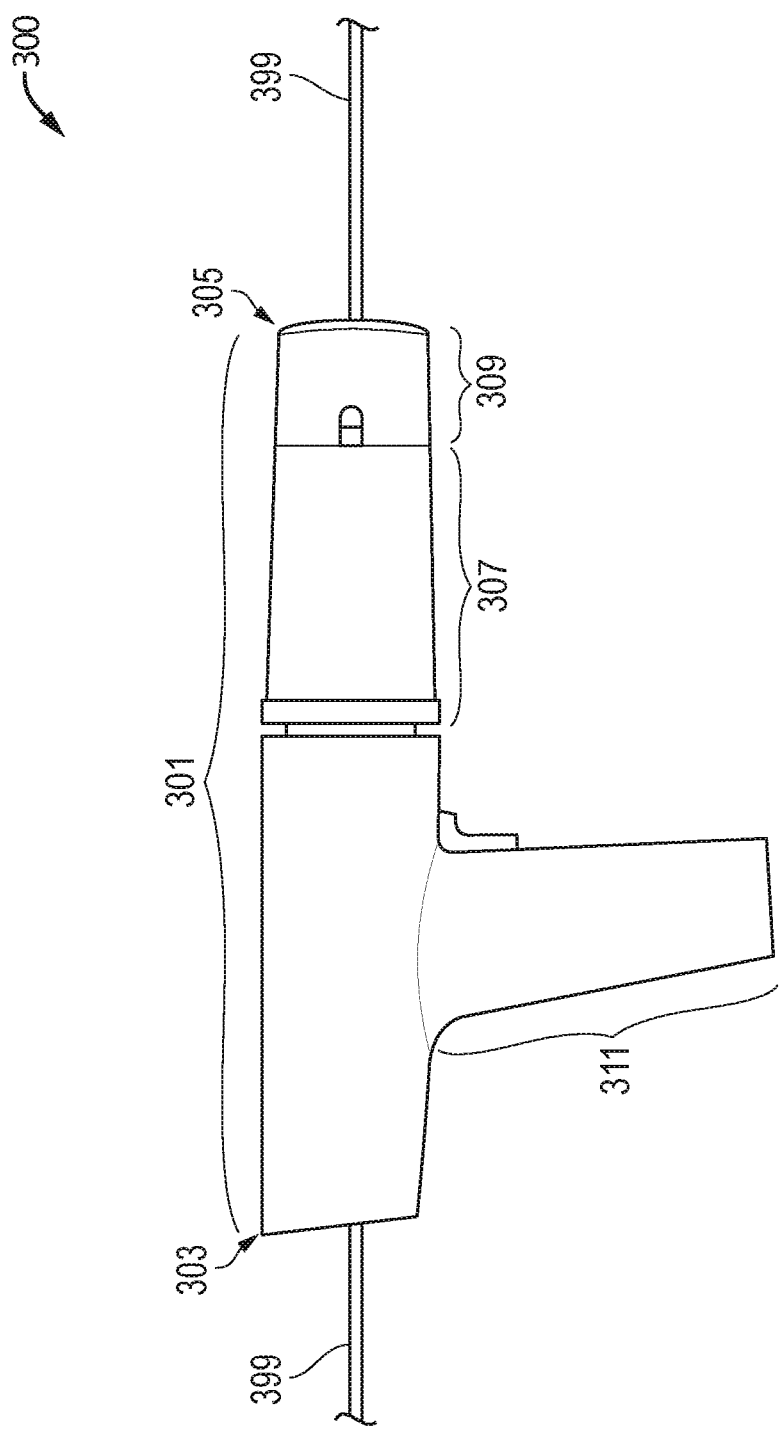
FIG. 35 includes a side view of a surgical tool with a guide wire extending through the interior in accordance with an embodiment.

The passage 1605 may align a larger passage that extends through the remainder of the tool 300. The passage 1605 may extend completely through the battery pack 1600, and the second passage may extend completely through the body of the surgical tool 300. These aligned passages are arranged to receive a guide wire 399 as illustrated in FIG. 35. The guide wire 399 can be threaded through the aligned passages and completely through the length of the tool 300. The tool 300 may then be precisely aligned relative to the patient through the guide wire 399. The relative sizes of the overall passage and the guide wire 399 provides for the tool 300 to move along the length of the guide wire 399 during the surgical procedure. The battery pack and tool bodies with aligned passages for use with the guide wire 399 may be used with the tool described above in FIGS. 1-17B, and may also be used in various other surgical tools including the POWEREASE tapper/driver tool from Medtronic Sofamor and Biologics of Memphis, Tenn.

FIGS. 18-26 include illustrations of a surgical tool according to another embodiment. In particular, certain components illustrated in FIGS. 18-26 illustrate a change to the coupling mechanism between the output shaft 315 and the motor 1913. Notably, the clutching mechanism described in accordance with previous embodiments included certain mechanical mechanism, while the following embodiments utilize certain other components, including for example, an electromechanical mechanism to accomplish coupling between the output shaft 315 and the motor 1913.

Figure 18:
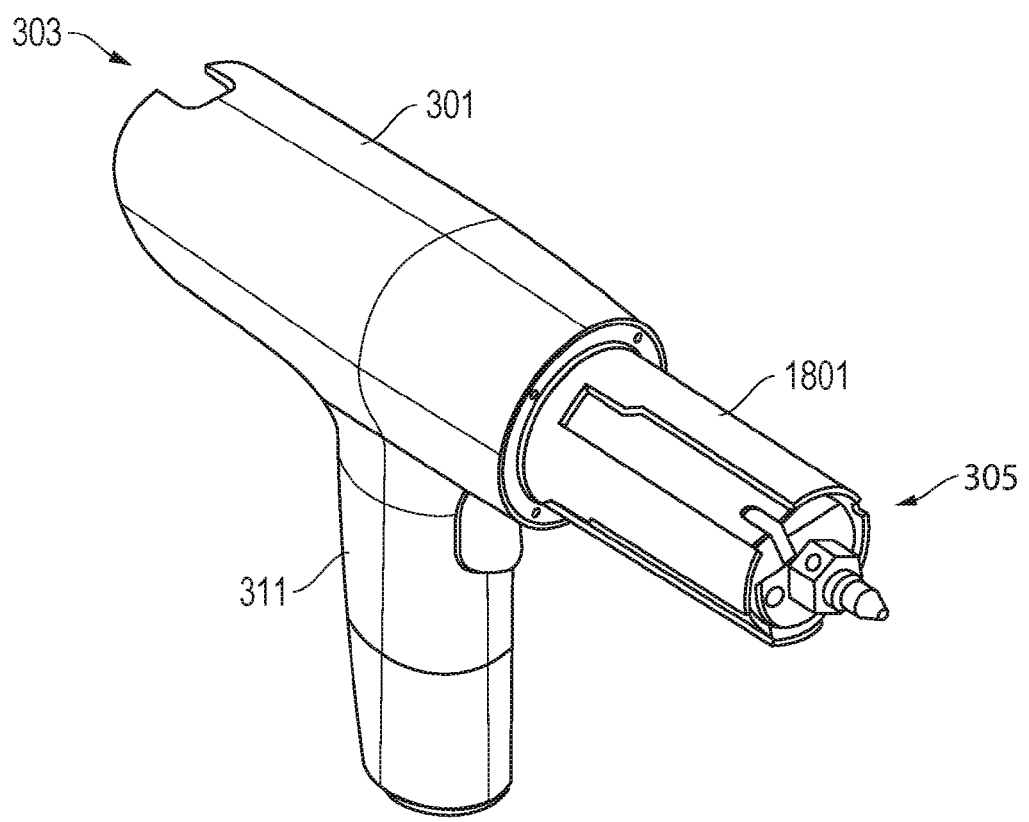
FIG. 18 includes a perspective view of a surgical tool according to another embodiment.

FIG. 18 includes a perspective view illustration of a surgical tool according to one embodiment. Like the tools described previously, the tool includes a housing 301 having a proximal end 303 and distal end 305. Additionally, the tool includes a handle portion 311 coupled to the housing 301 and extending in a direction substantially perpendicular to a longitudinal axis of the housing 301. Moreover, unlike previous embodiments, the tool includes an inner sleeve 1801 having particular surface features that facilitate clutching as will be described in more detail in the following figures.

Figure 19:
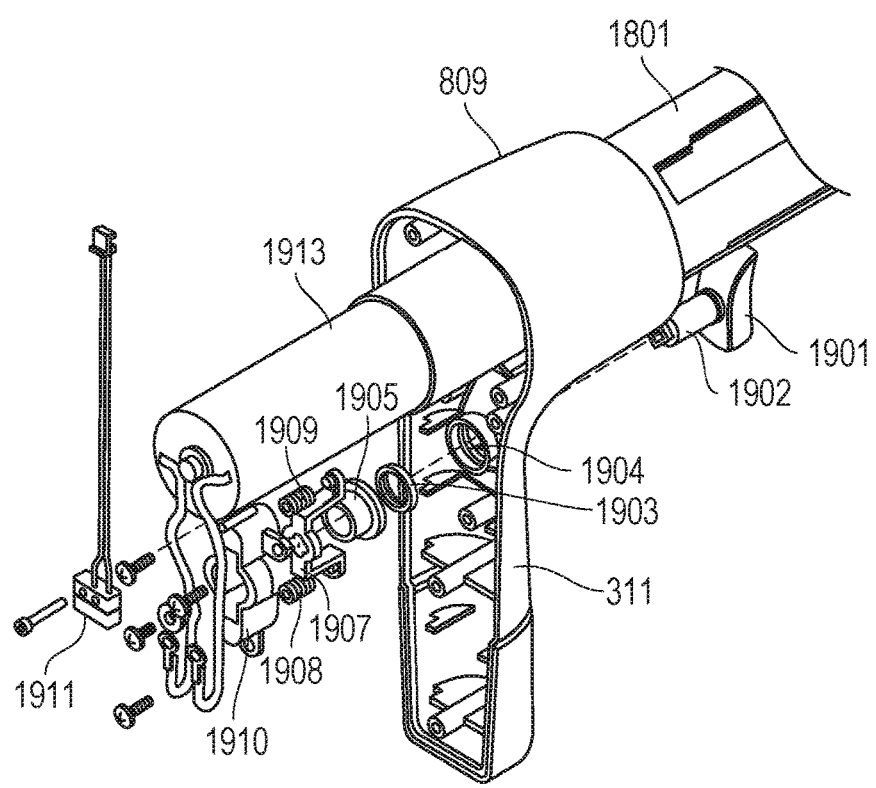
FIG. 19 includes a perspective view of a portion of a surgical tool and certain components within the tool in accordance with an embodiment.

FIG. 19 includes a perspective view of a portion of the tool in accordance with an embodiment. As illustrated, the tool includes a housing portion 809 proximal to the distal end of the tool and an inner sleeve 1801 coupled to and extending from the housing portion 809. The inner sleeve 1801 can be formed with the housing portion 809 such that the two components form a single, monolithic piece. Alternatively, the inner sleeve 1801 can be coupled to the housing portion 809 via fasteners, interference fit coupling, snap-fit coupling mechanism, or the like.

As further illustrated in FIG. 19, the tool includes a trigger 1901 having a shaft portion 1902 that is configured to be engaged within an opening 1904 of the handle portion 311, such that the trigger 1901 is coupled to the housing portion 809. The trigger mechanism can include other components as illustrated, notably a shaft seal 1903 configured to engage and directly contact the shaft portion 1902 within the handle portion 311. The trigger mechanism further includes a bearing member 1905 configured to engage the shaft portion 1902 within the handle portion 311 and facilitate translation of the shaft portion 1902 within the trigger mechanism during operation of the trigger by a user. A bracket 1907 can be used to secure and couple the bearing member 1905, shaft seal 1903, and trigger shaft 1902 together within the handle portion 311.

The bracket 1907 can be coupled to a trigger mounting 1910 that facilitates coupling of the bracket 1907, bearing member 1905, and shaft seal 1903 to the interior of the handle portion 311. The bracket 1907 can be biased against the trigger mounting 1910 via biasing members 1908 and 1909 that facilitate biasing the position of the trigger 1901 into a position until the trigger is depressed by a user. Accordingly, biasing members assure that the trigger is maintained at a starting position (i.e., off position) until the mechanism is acted upon by a force, such as by a users finger.

Notably, the trigger mechanism includes a trigger switch 1911 that is coupled to the trigger mounting 1910. The trigger switch 1911 can be a high-temperature switching component, capable of withstanding temperatures akin to autoclaving environments. The trigger switch 19111 can be electrically connected to the motor 1913, such that upon movement of the trigger 1901 from a first position (i.e., starting position) to a second position (i.e., a depressed position), the shaft portion 1902 is translated laterally into the interior of the handle portion 311 and the trigger switch 1911 is actuated. According to one embodiment, actuation of the trigger switch 1911 by the trigger 1901 changes the state of the trigger switch 1911 from an off state to an on state. In more particular instances, at the on state, a closed circuit can be formed between the motor 1913 and the trigger switch 1911 such that current is flowing between the two components, and the motor 1913 is operable. When the motor 1913 is operable, it is capable of rotating the output shaft 315. According to one embodiment, when the trigger switch 1911 is at an on state, if another condition is met with regard to the clutching assembly, the motor 1913 can be operable.

Figure 20:
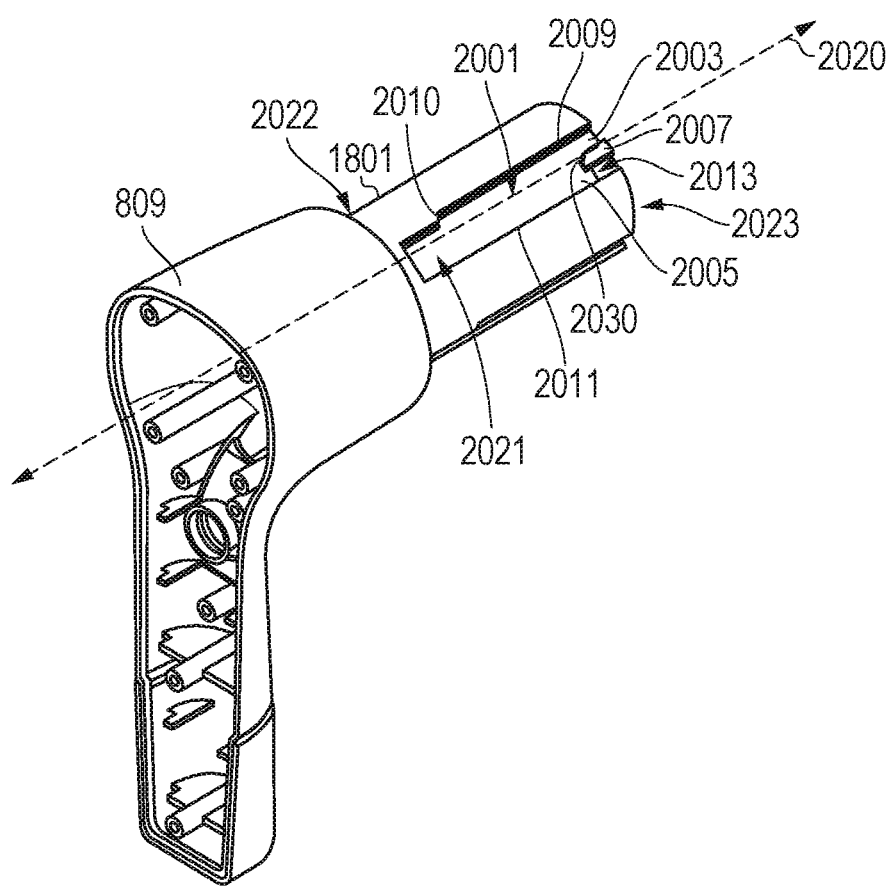
FIG. 20 includes a perspective view of a portion of a surgical tool including an inner sleeve in accordance with an embodiment.

FIG. 20 illustrates a perspective view of a portion of a surgical tool in accordance with an embodiment. In particular, FIG. 20 illustrates the housing portion 809 and inner sleeve 1801 extending axially from the housing portion 809 in a direction of the longitudinal axis 2020. As illustrated, the inner sleeve 1801 can include a surface feature, such a recess 2001 that extends generally along the longitudinal axis 2020 and the exterior surface of the inner sleeve 1801. In certain embodiments, the inner sleeve 1801 can include more than one recess, such as a series of recesses that extend axially along the longitudinal axis 2020 of the inner sleeve 1801. Particular embodiments utilize at least about 2 recesses and not greater than about 5 recesses depending upon the size of the inner sleeve 1801.

The recess 2001 can have an asymmetrical shape comprising a first surface 2011 extending axially along a direction of the longitudinal axis 2020, and comprising a second surface 2009 extending substantially along the same direction as the longitudinal axis 2020, and further including a tapered surface 2010 extending at an angle with respect to the surface 2009. The recess 2001, and particularly the tapered surface 2010, can define a minor recess area 2021 near the proximal end 2022 of the inner sleeve 1801 within the recess 2001. The asymmetrical shape of the recess 2001 facilitates suitable engagement of an outer sleeve on the inner sleeve 1801, and more particularly, engagement of features within the interior of the outer sleeve in the recess 2001 such that upon movement of the outer sleeve with respect to the inner sleeve 1801, the features within the interior of the outer sleeve engage certain surfaces of the recess 2001 as will be described in more detail herein.

The inner sleeve 1801 further includes an island 2007 disposed within the recess 2001 and extending from a distal end 2023 in a direction of the longitudinal axis 2020 along the inner sleeve 1801. As illustrated, the island 2007 extends for a discrete distance along the exterior surface of the inner sleeve 1801 within the recess 2001. The island 2007 can have a generally rectangular contour, and in particular, includes a tapered surface 2030 that facilitates movement of features within the interior of the outer sleeve about either side of the island 2007 within the recess 2001.

As illustrated in FIG. 20, the island 2007 that separates two regions of the recess 2001 and therein defines two different grooves within the recess 2001, notably an inactive groove 2003 and an active groove 2005. The inactive groove 2003 and active groove 2005 generally extend axially within the recess 2001 along a direction of the longitudinal axis 2020 of the inner sleeve 1801 and are laterally spaced apart from each other. In particular, the inactive groove 2003 is defined as the region between surfaces 2009 and 2010, and the island 2007. The inactive groove 2003 facilitates initial coupling between an outer sleeve and the inner sleeve 1801 and engages features on the interior surface of the outer sleeve when the tool is in an inactive state, that is, when the motor 1913 is not operable and incapable of rotating the output shaft 315. The active groove 2005 is defined as the region between the surface 2011 and the island 2007 and is configured to engage surface features within the interior of the outer sleeve when the tool is in an active state, that is, when the motor 1913 is operable and capable of rotating the output shaft 315.

As further illustrated, the recess 2001 includes an opening 2013 extending axially along the direction of the longitudinal axis 2020 from a distal end 2023 of the inner sleeve 1801. In particular, the opening 2013 is disposed within the active groove 2005 at the distal end 2023 of the inner sleeve 1801. The opening 2013 facilitates engagement of a portion of an actuator arm therein, such that upon movement of an outer sleeve from a first position to a second position with respect to the inner sleeve 1801, the portion of the actuator arm within the opening 2013 is engaged by surface features within the interior of the outer sleeve.

Figure 21:
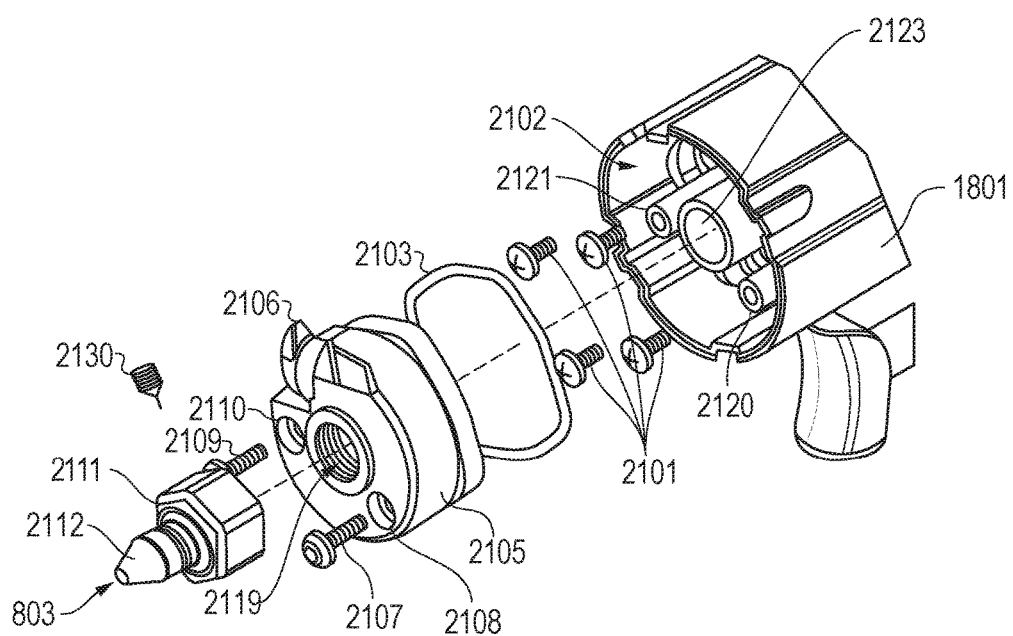
FIG. 21 includes a perspective view of a portion of a surgical tool including certain components within the tool in accordance with an embodiment.

Features of the actuator arm are more clearly illustrated in FIGS. 21-24. FIG. 21 includes a perspective view illustrating a portion of a surgical tool including certain components within the tool in accordance with an embodiment. FIG. 21 includes an illustration of particular components designed to fit within an interior space 2102 at the distal end of the inner sleeve 1801 according to one embodiment. Some of the components include a seal member 2103, a cap member 2105 housing the seal member 2108, and an actuator arm 2106 configured to engage the cap member 2105 within the interior space 2102. Other components include a motor shaft portion 803 including a base portion 2111, and a head portion 2112 coupled to the base portion 2111. The motor shaft portion 803 is configured to be engaged within an opening 2119 of the cap member 2105 and further configured to engage a drive shaft of the motor 1913 through an opening 2123 within the interior space 2102 of the inner sleeve 1801, such that upon rotation of the drive shaft, the motor shaft portion 803 is rotated.

The interior space 2102 of the distal end of the inner sleeve 1801 can include fasteners 2101 designed to be threaded into corresponding openings within the interior space 2102 for engagement with and fixation of the motor 1913 within the inner sleeve 1801. The seal member 2103 can be placed within the interior space 2102 of the inner sleeve 1801 to form a seal between the portion of the inner sleeve housing the motor 1913, and the portion of the inner sleeve housing the cap member 2105 and other components illustrated in FIG. 21. In particular, the seal member 2103 facilitates use of the tool as a surgical tool, capable of being exposed to high temperatures, pressures, and even liquids typically used to sterilize components for use in an operatory. For example, the tool must be able to withstand environments used in autoclaving, a common method of sterilizing surgical tools. Moreover, the seal member 2103 avoids access of bodily fluids typically encountered in surgical procedures from entering the portion of the inner sleeve 1801 housing the motor 1913.

The cap member 2105 is configured, to be engaged within the interior space 2102 of the inner sleeve 1801 and can be affixed to the inner sleeve 1801 via fasteners 2107 and 2109 that can be engaged within openings 2108 and 2110 within the cap member 2105, and in turn further engage openings 2120 and 2121 within the inner sleeve 1801. Notably, the cap member 2105 houses the actuator arm 2106, and according to the illustrated embodiment, a portion of the actuator arm 2106 extends from the cap member 2105 in a direction substantially perpendicular to the longitudinal axis of the inner sleeve 1801. The orientation between actuator arm 2106 and cap member 2105 facilitates protrusion of a portion of the actuator arm into the opening 2013 within the active groove 2005 of the inner sleeve 1801.

The motor shaft portion 803 includes a base portion 2111 coupled to the head portion 2112 configured to be engaged with the cap member 2105 within the inner sleeve 1801. In particular, the motor shaft portion 803 is configured to be engaged with the cap member 2105 and a portion of the motor 1913 through the opening 2119 within the cap member 2105. The base portion 2111 and head portion 2112 can be a single, monolithic member, or alternatively, can be two discrete components that are coupled together. Moreover, as further illustrated and according, to one embodiment, the motor shaft portion 803 can be coupled to a drive shaft of the motor 1913 via a fastener 2130, such as a set screw.

Figure 22:
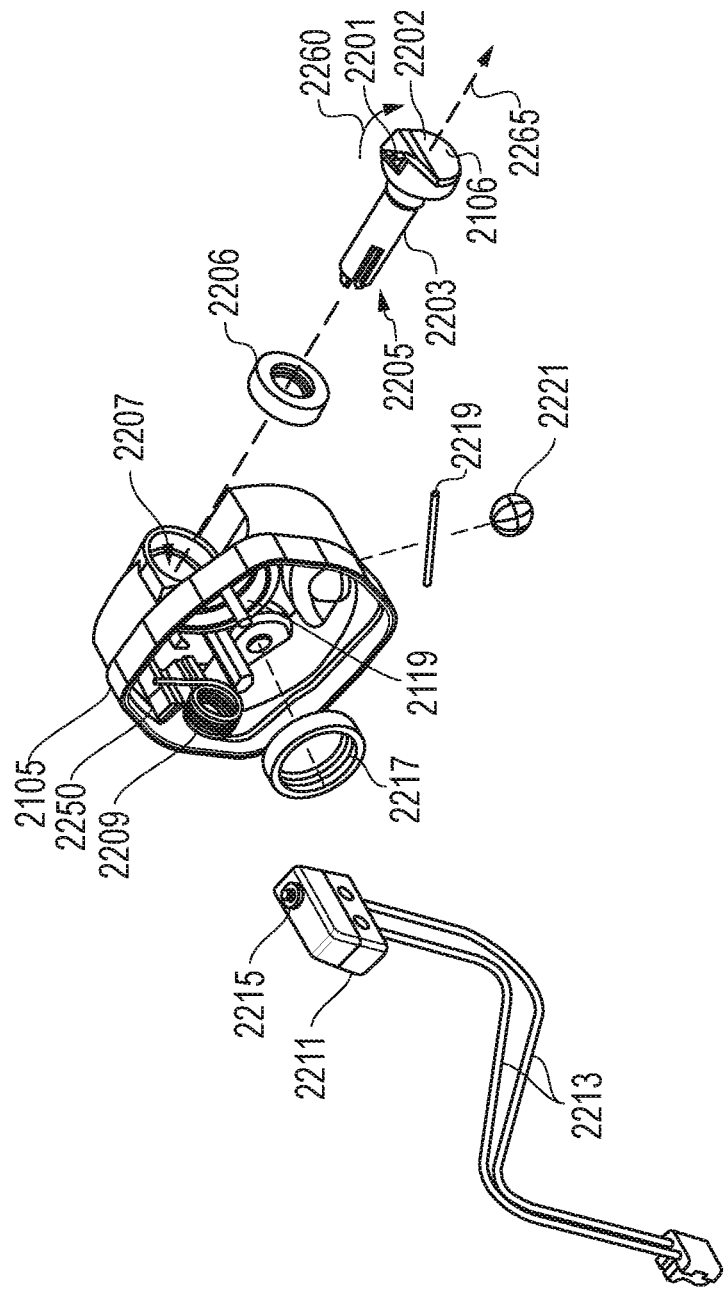
FIG. 22 includes a perspective view of a cap portion and certain components within the cap portion in accordance with an embodiment.
Figure 23:
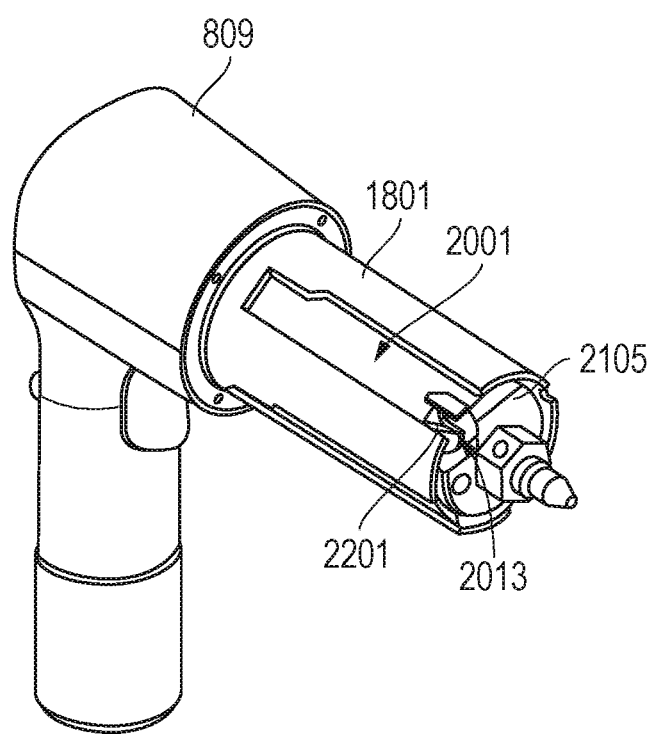
FIG. 23 includes a perspective view of a portion of the tool including the inner sleeve and cap portion as assembled in accordance within an embodiment.

FIG. 22 includes a perspective view of a cap member and certain components within the cap member in accordance with an embodiment. The cap member 2105 can include a seal 2217 configured to be engaged within the opening 2119 suitable for sealing the connection between the output shaft of the motor 1913 and the motor shaft portion 803. Additionally, the cap member 2105 includes a ball member 2221 configured to be engaged within an outer surface of the cap member 2105 to facilitate releasable engagement with a collar (See FIG. 26). Notably, the ball member 2221 can be biased into a position by a biasing member 2219 to facilitate releasable engagement between the cap member 2105 and the collar.

As illustrated, the cap member 2105 can include an opening 2207 disposed at an outer surface and at an orientation that is substantially perpendicular to the longitudinal axis of the inner sleeve 1801. The actuator arm 2106 is configured to engage and extend through the opening 2207 of the cap member 2105, and can include a head portion 2202 attached to a shaft portion 2203. The head portion 2202 can include a fin 2201 (e.g., a protrusion) extending from the head portion 2202 that is configured to be engaged within the opening 2013 of the recess 2001 within the inner sleeve 1801. The shaft member 2203 is further positioned within the opening 2207 of the cap member 2105 such that the shaft is disposed within the interior of the cap member 2105. The shaft portion is configured to engage a seal member 2206 that can be contained within the interior of the cap member 2105 such that contaminates do not penetrate the interior of the cap member and also such that the tool is suitable for sterilization.

A biasing member 2209 can be provided around the end of the shaft portion 2203 of the actuator arm 2106 such that a biasing force is provided to the actuator arm 2106 and the actuator arm 2106 is resiliently biased to a particular orientation as illustrated in FIG. 22. Notably, the orientation can include positioning of the fin 2201 in an upright position such that it protrudes into the opening 2013 within the recess 2001 of the inner sleeve 1801. This arrangement is more clearly illustrated in FIG. 23, which provides a perspective view of a portion of the tool including the inner sleeve 1801 and cap member 2105 as assembled in accordance within an embodiment is illustrated. As shown, the cap member 2105 is assembled within the interior space at the distal end of the inner sleeve 1801, and more particularly, the fin 2201 of the actuator arm 2106 is positioned within the opening 2013 of the recess 2001 at a biased, upright position.

Referring again to FIG. 22, the cap member 2105 can further include a clutching switch 2211 disposed within the interior of the cap member 2105. In particular, the clutching switch 2211 can be disposed within a location 2250 such that it is disposed against an interior wall of the cap member 2105 and positioned proximate to the end of the shaft portion 2203 of the actuator arm 2106. The clutching switch 2211 can be a high temperature switching component, capable of withstanding temperatures and pressures akin to autoclaving environments. The clutching switch 2211 can include an actuator 2215 such that upon movement of the actuator from a first position to a second position the clutching switch 2211 changes states, such as from an off state to an on state, or more particularly from an open circuit to a closed circuit. As illustrated and according to one embodiment, the actuator 2215 can be a button that is depressed. Other actuators for changing the state of the clutching switch can be used, such as for example levers, dials, and the like. The clutching switch 2211 can include wires 2213 electrically connecting the switch to the motor 1913.

During operation of the tool, the actuator arm 2106, and more particularly, the fin 2201 can be moved between a first position and a second position. Notably, movement of the fin 2201 can include rotation of the actuator arm 2106 about the axis 2265 in the direction 2260 such that the shaft portion 2203 of the actuator arm 2106 is rotated within the cap member 2105. Rotation of the shaft portion 2203 can result in a tapered region 2205 of the shaft portion 2203 engaging the actuator 2215 of the clutching switch 2211. As such, movement of the actuator arm 2106 between the first position and the second position results in a change of state of the clutching switch 2211. For example, according to one embodiment, the clutching switch 2211 can change from an off state to an on state upon movement of the actuator arm 2106 between the first position and the second position. The on state can include the formation of a closed circuit between the motor 1913 and the clutching switch 2211 such that the motor is in an operable state, that is, the motor 1913 is capable of rotating the output shaft 315.

The amount of rotation of the shaft portion 2203 is engineered such that the component cannot be accidentally rotated to a degree to cause inadvertent engagement of the actuator 2215, putting the tool in an operable state, which may be particularly hazardous in the context of surgical procedures. In particular embodiments, the degree of rotation of the shaft portion 2203 of the actuator arm 2106 suitable to engage the actuator 2215 of the clutching switch 2211 is not greater than about 180 degrees. For example, certain designs utilize a degree of rotation of the shaft portion that is nm greater than about 160 degrees to engage the actuator arm. In other embodiments, the degree of rotation can be less, for example, not greater than about 90 degrees, and particularly within a range between about 20 degrees and about 90 degrees, and more particularly between about 20 degrees and about 70 degrees.

As stated previously, the trigger switch 1911 can function in a same or similar manner, that is, forming a closed circuit between the motor 1913 and trigger switch 1911 and thus facilitating operation of the motor 1913 if another condition is met. In particular, the foregoing describes the previously mentioned condition for operation of the motor. Accordingly, when the actuator arm 2106 is rotated to a position sufficient to engage the actuator 2215 of the clutching switch 2211 a closed circuit can be formed between the clutching switch 2211 and motor 1913. Additionally, the trigger switch 1911 can be actuated by a user such that a closed circuit is formed between the trigger switch 1911 and the motor 1913. When the foregoing conditions are met, the motor is in an operable state and capable of rotating the output shaft 315. In particular embodiments, if one of the two switches (i.e., clutching switch 2211 or trigger switch 1911) is not actuated such that a closed circuit is not formed between either of the clutching switch 2211 and motor 1913 or trigger switch 1911 and motor 1913, the motor 1913 can be inoperable, and may not be capable of rotating the output shaft 315. The foregoing describes an electromechanical clutching mechanism. Such a design may facilitate a smaller, light-weight tool incorporating less components than designs using primarily mechanical clutching mechanisms.

Figure 24:
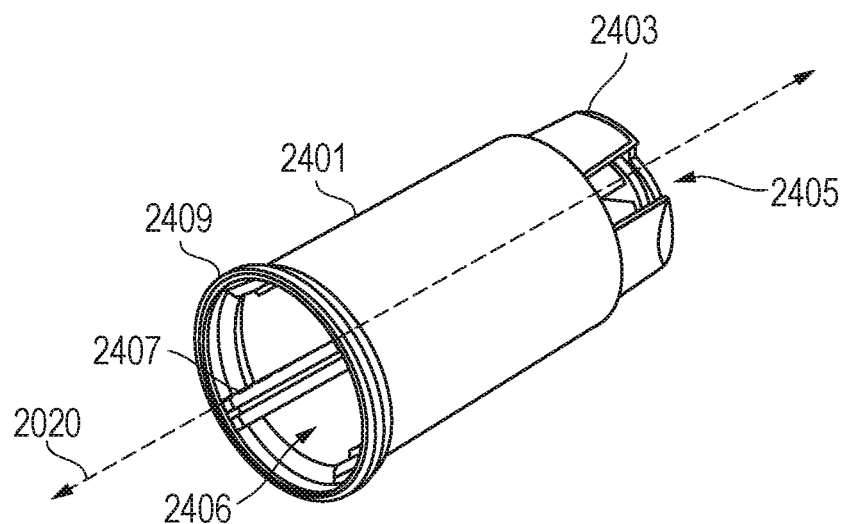
FIG. 24 includes a perspective view of an outer sleeve in accordance with an embodiment.
Figure 25:
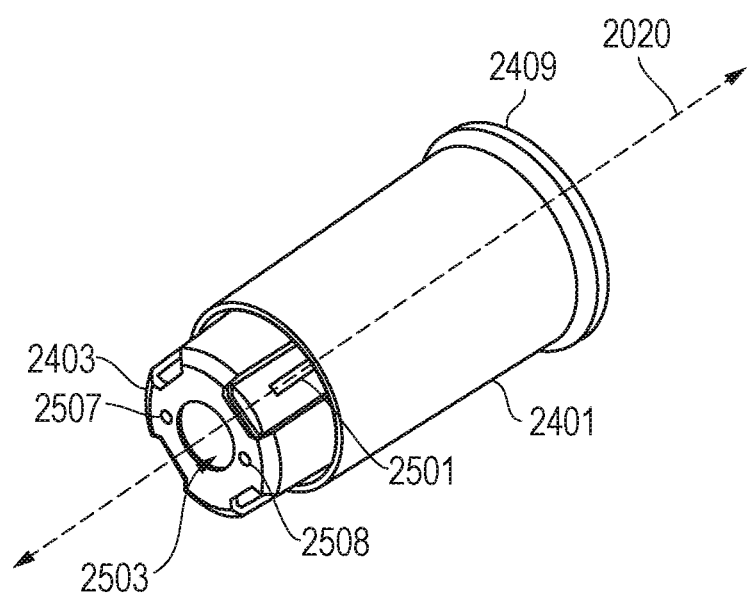
FIG. 25 includes a perspective view of an outer sleeve in accordance with an embodiment.
Figure 26:
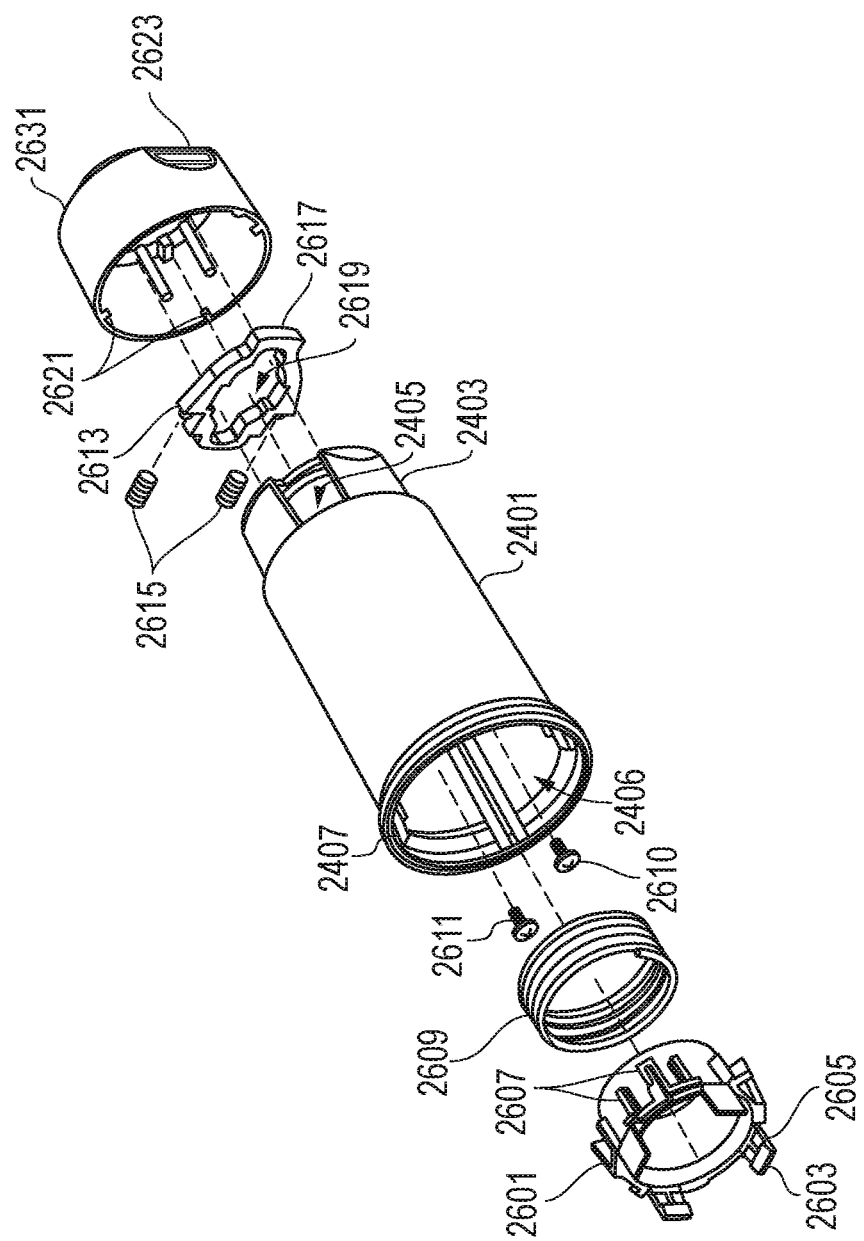
FIG. 26 includes a perspective view of the outer sleeve and associated components for use in the tool in accordance with an embodiment.

Referring now to FIGS. 24-26, the outer sleeve and associated components, which have been made reference to previously, are described in more detail. FIG. 24 includes a perspective view of an outer sleeve in accordance with an embodiment. The outer sleeve 2401 is configured to fit over the inner sleeve 1801 such that inner sleeve 1801 is engaged within an interior space 2406 of the outer sleeve 2401. As illustrated, the outer sleeve 2401 can have a substantially cylindrical shape and include a rim 2409 extending around the circumference of the outer sleeve 2401 abutting the proximal end of the outer sleeve 2401. The outer sleeve 2401 can further include a head portion 2403 at a distal end of the outer sleeve 2401, wherein the head portion 2403 includes openings 2405 radially space apart around the circumference and configured to facilitate coupling of the inner sleeve 1801 and the inner coupling portion 611.

The outer sleeve 2401 can further includes rails 2407 extending axially in the direction of the longitudinal axis 2020 within the interior surface of the outer sleeve 2401. According to one embodiment, the rails 2407 can aid initial engagement of the outer sleeve 2401 with the inner sleeve 1801, such that the outer sleeve 2401 can slideably engaged the exterior surface of the inner sleeve 1801 by engaging the rails 2407 within the recess 2001. More particularly, the rails 2407 may be used to engage the inactive groove 2003 of the recess 2001 for initial coupling between the inner sleeve 1801 and the outer sleeve 2401. In certain embodiments, the outer sleeve 2401 can include a plurality of rails, such as not less than about 3 or even not less than about 4 groups of rails, extending along the interior surface of the outer sleeve 2401 for engagement with complementary recesses within the inner sleeve 1801.

FIG. 25 includes another perspective view of the outer sleeve of FIG. 24 in accordance with an embodiment. Notably, FIG. 25 illustrates a protrusion 2501 that extends axially along an interior surface of the outer sleeve 2401 in a direction along the longitudinal axis 2020, and further extends from the interior surface of the outer sleeve 2401 into the interior space 2406 of the outer sleeve 2401. The protrusion 2501 can be connected to one of the rails 2407, such that it extends from an end of a rail for a length along the longitudinal axis 2020. Moreover, in certain embodiments using a plurality of rails, the outer sleeve 2401 can include a plurality of protrusions, wherein each of the protrusions of the plurality of protrusions is attached to a corresponding set of rails.

In certain instances, the protrusion 2501 can be a single protrusion, or alternatively, there can be more than one protrusion. For example, in one embodiment, the protrusion 2501 can include two protrusions. In particular embodiments, one protrusion can have a length that is greater than a length of the other protrusion, wherein length is measured by the distance extending in a direction of the longitudinal axis of the outer sleeve 2401. In such instances, the shorter protrusion can be configured to engaged the island 2007 when the protrusions are engaged within the inactive groove 2003 and engaged the surface 2011 when the protrusions are engaged within the active groove 2005. Moreover, in certain instances using two protrusions of different lengths, one of the protrusion (shorter) can be configured to engage the fin 2201 of the actuator arm 2106 while the other protrusion (longer) can be a torque-bearing protrusion bearing the majority of torque forces against the surface 2011.

The rails and protrusion 2501 are particularly integrated such that the protrusions can be more closely spaced together relative to each other in a lateral direction than the rails 2407 are spaced together relative to each other. In fact, certain embodiments utilize protrusions that are abutting one another in a side-by-side orientation. This design facilitates the formation of a corner, otherwise a lateral offset, at the connection between the protrusion 2501 and the tails 2407. In more particular designs, the protrusion 2501 consists of a short protrusion and a long protrusion and the rails 2407 comprise two rail elements extending longitudinally along the inner surface of the outer sleeve 2401 parallel to each other. One of the protrusions (e.g., the short protrusion) can extend along the same axis of one of the tail elements, while the other protrusion (e.g., long protrusion) is abutting the other protrusion, and thus is laterally offset from the axis of the other rail element to form a corner at the connection between said particular rail element and said (long) protrusion. As such, during actuation of the outer sleeve relative 2401 to the inner sleeve 1801, once the protrusion(s) 2501 are engaged within the active groove 2005, the outer sleeve 2401 can be translated toward the distal end 305 of the tool for a distance until the corner engages the island 2007 thus stopping the degree of translational motion and maintaining the outer sleeve 2401 on the inner sleeve 1801.

As illustrated in FIG. 25, the outer sleeve 2401 further includes an opening 2503 in the head portion 2403 for engagement of the output shaft 315 therein. Moreover, the head portion 2403 includes openings 2507 and 2508 for engagement of fasteners therein for affixing the inner coupling portion 611 to the head portion 2403.

FIG. 26 includes a perspective view of the outer sleeve and associated components for use in the tool in accordance with an embodiment. As illustrated, the outer sleeve 2401 can include a collar 2601 configured to be disposed within the interior space 2406 of the outer sleeve 2401. According to one embodiment, the collar 2601 can have a generally cylindrical shape such that it can be fitted within the head portion 2403 of the outer sleeve 2401. Notably, the collar 2601 can include a series of projections 2607 extending from the exterior surface of the collar along the direction of the longitudinal axis 2020 of the outer sleeve 2401. The projections 2607 are configured to be engaged within complementary features within the inner coupling portion 611. In particular embodiments, the complementary features can be tabs 2621 disposed within the inner surface of the inner coupling portion 611.

The collar 2601 can further include teeth 2603 extending from a proximal end of the collar along the direction of the longitudinal axis 2020. The teeth 2603 can be radially spaced apart along the circumference of the collar 2601. Additionally, in certain embodiments, the teeth 2603 can have surface features suitable for engaging portions of the inner sleeve 1801. For example, according to the illustrated embodiment, the teeth 2603 can have complementary surface features, such as depressions 2605 for engaging portions of the inner sleeve, such as the ball member 2221 disposed along the outer surface of the cap member 2105. The ball member 2221 can be biased into a position such that upon engagement with one of the teeth 2603 of the collar 2601, the ball member 2221 is urged to rest within the complementary depression until enough force is exerted on the collar 2601 to release the collar 2601 and cap member 2501 from each other.

The outer sleeve 2401 can further include a biasing member 2609 configured to be disposed within the interior space 2406 of the outer sleeve 2401. In particular, the biasing member 2609 can contact an interior surface of the outer sleeve 2401 at the distal end within the head portion 2403. The biasing member 2609 biases the translational motion between the outer sleeve 2401 and inner sleeve 1801 utilized for engagement of the actuator arm 2106 that operates the clutching mechanism. In particular, the biasing member 2106 biases the two components (i.e., the outer sleeve 2401 and inner sleeve 1801) into an initial unengaged state (i.e., the clutching switch is disengaged), which the user can overcome via a rotational movement of the outer sleeve 2401 followed by a translational movement of the outer sleeve 2401 toward the distal end 305 of the tool to affect engagement of the actuator arm 2106 and thus the clutching switch 2211.

As further illustrated in FIG. 26, a locking member 2613 can be coupled to the outer sleeve 2401. In particular, the locking member 2613 is configured to releasably engage the counter-torque sleeve 313 from a coupling portion 2631. The locking member 2613 includes a central opening 2619 in the body having a particular shape to engage the proximal end of the counter-torque sleeve 313 therein. The locking member 2613 can be coupled to the exterior surface of the outer sleeve 2401 at the head portion 2403 and contained within the interior of the coupling portion 2631. In accordance with one embodiment, the locking member 2613 can be coupled with grooves along the interior surface of the coupling portion 2631 and may be a "floating" component, wherein it is not fixably locked into a position, and rather, compressed between the head portion 2403 and interior surface of the coupling portion 2631.

According to one embodiment, the locking member 2613 includes a projection 2617 extending from the locking member body and configured to extend from an opening 2623 within the inner coupling member 2611. The extension of the projection 2617 allows for releasable engagement of the counter-torque sleeve 313, as the projection 2617 can be depressed to facilitate release of the counter-torque sleeve 313 from the coupling portion 2631. As will be appreciated, biasing members 2615 bias the position of the projection 2617 such that it extends through the opening 2623 until engaged by a user.

The coupling portion 2631 can be coupled to the outer sleeve 2401 at the head portion 2403, such that the coupling portion 2631 extends over substantially the entire surface of the head portion 2403 covering the openings 2405. The coupling portion 2631 can be fixably attached to the head portion 2403 of the outer sleeve 2401 via fasteners 2610 and 2611, which may be threaded from the interior of the outer sleeve 2401.

Figure 27A:
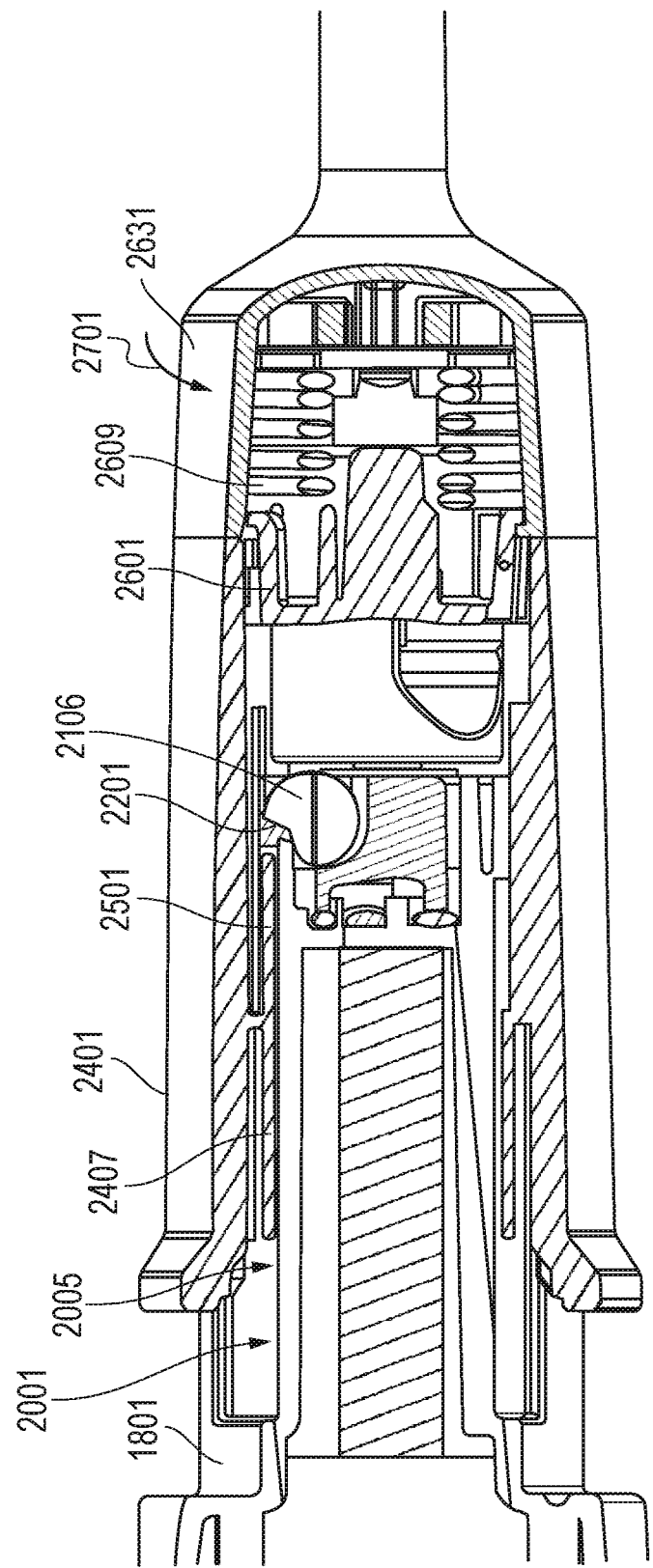
FIG. 27A and FIG. 27B include cross-sectional illustrations of a portion of the tool including the outer sleeve and actuator arm in a disengaged state and in an engaged state according to an embodiment.
Figure 27B:
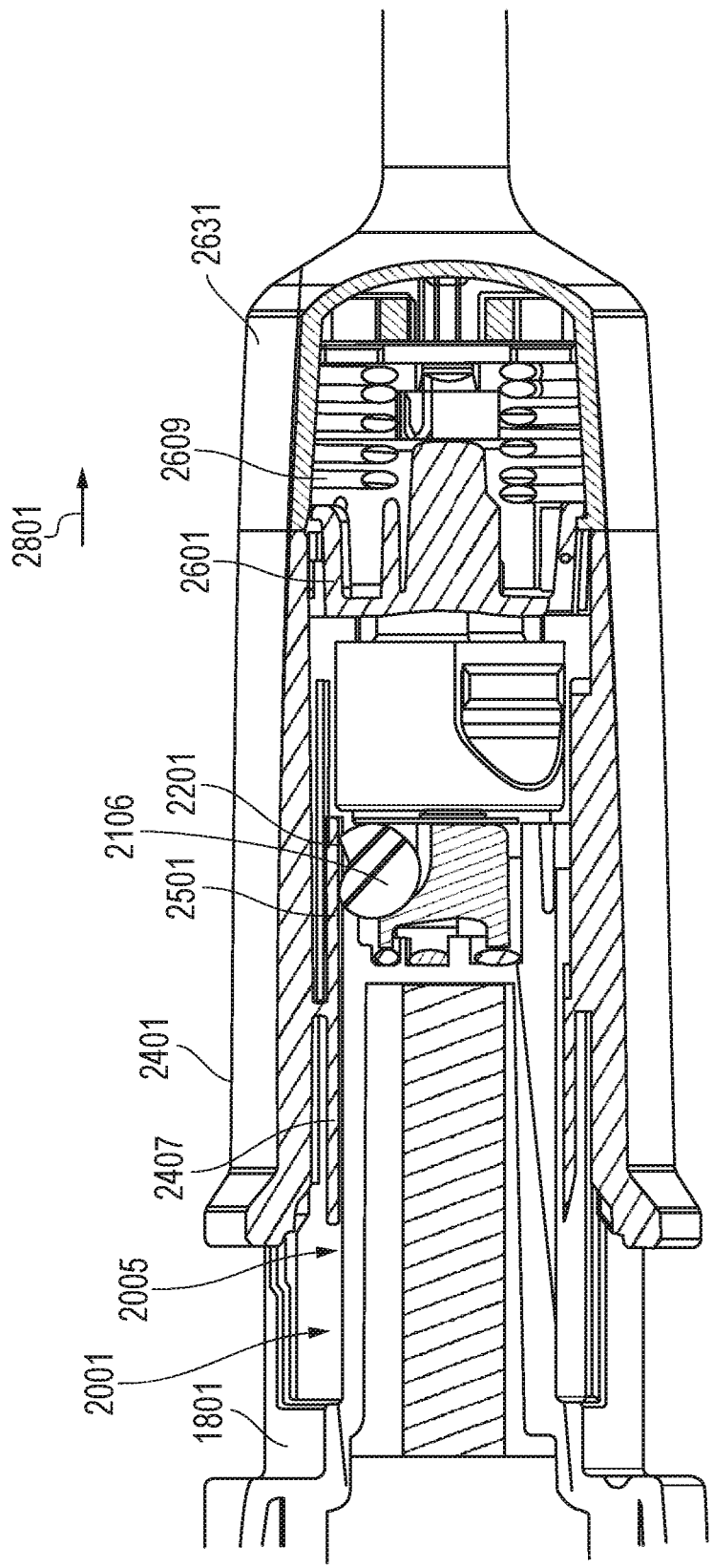

FIGS. 27A and 27B illustrate actuation of the clutching switch 2211, and more particularly, the actuation of the fin 2201 of the actuator arm 2106 during operation of the outer sleeve 2401. FIG. 27A includes a cross-sectional illustration of a portion of the tool including the outer sleeve and actuator arm in a disengaged state according to an embodiment. As illustrated, the outer sleeve 2401 is overlying the inner sleeve 1801. The outer sleeve 2401 includes protrusion 2501 extending from the rail 2407 along the inner surface of the outer sleeve 2401. In an initial and unengaged state of the tool, the rail 2407 is not in the active groove 2005 and the biasing member 2609 is configured to act against an inner surface of the head portion 2403 against the collar 2601 to bias the outer sleeve 2401 in a back and neutral state. In order to move the actuator arm 2106, a user may move the outer sleeve 2401 by first rotating the outer sleeve 2401 in a direction 2701 until the rail 2407 abuts the first surface 2011 of the recess 2001 and is engaged in the active groove 2005. Such an action also places the protrusion 2501 within the active groove 2005 of the recess such that it is positioned directly behind the fin 2201 of the actuator arm 2106 as illustrate in FIG. 27A.

Referring now to FIG. 27B, a cross-sectional illustration of a portion of the tool including the outer sleeve and actuator arm in an engaged state is provided according to an embodiment. As illustrated in FIG. 27B, after sufficiently rotating the outer sleeve 2401 to the position illustrated in FIG. 27A, the user can translate the outer sleeve 2401 relative the inner sleeve 1801 in the direction 2801 toward the distal end 305 of the tool. The translation of the outer sleeve 2401 facilitates translation of the protrusion 2501 to the position illustrated in FIG. 27B, wherein the protrusion 2501 is engaged with the fin 2201 and the actuator arm 2201 is rotated to a second position as illustrated. As described herein, rotation of the actuator arm 2201 to the second position facilitates changing the state of the clutching switch 2211 from an off position to an on position, which in turn can turn the motor 407 to an on position allowing the user to operate the tool. As will be appreciated, to disengage the motor, the outer sleeve can be returned to its initial unengaged position by translating the outer sleeve 2401 in the direction opposite the direction 2801 and rotating the outer sleeve 2401 in a direction opposite the direction 2701.

According to certain embodiments, the rotational movement suitable for engaging the clutching mechanism can be not greater than about 90 degrees, such as not greater than about 70 degrees, or even for example, not greater than about 60 degrees, 50 degrees, or 30 degrees. Particular embodiments utilize a rotational motion within a range between about 5 degrees and about 90 degrees, such as within a range between about 5 degrees and about 60 degrees, in certain instances between about 5 degrees and about 30 degrees, and more particularly within a range between about 5 degrees and about 25 degrees.

Moreover, the degree of translational movement suitable for engaging the actuator arm 2201 can be considered the engagement distance and can generally be not greater than about 20% of the total length of the inner sleeve 1801. In other embodiments, the engagement distance is less, such as not greater than about 15%, such as not greater than about 10%, and even not greater than about 8% Particular embodiments utilize an engagement distance of at least about 2%, or even at least about 4%. For example, the engagement distance can be within a range between about 3% and about 20%, and more particularly within a range between about 3% and about 10% of the total length of the inner sleeve 1801.

The foregoing has made reference to use of actuators and engagement of mechanical components for changing the state of the tool, particularly from a state in which the output shaft may not be rotated to a state wherein the output shaft can be rotated. Still, other embodiments can utilize a different type or different combination of components to achieve such results. For example, embodiments herein can include a tool that utilizes magnetic devices, electronic devices, and a combination thereof for operation of the tool. The magnetic devices described herein can be used in conjunction with any other devices (e.g., switches, actuators, etc.) previously described herein. Alternatively, the magnetic devices described herein can be used without the use of other such devices described in the other embodiments.

Figure 28:
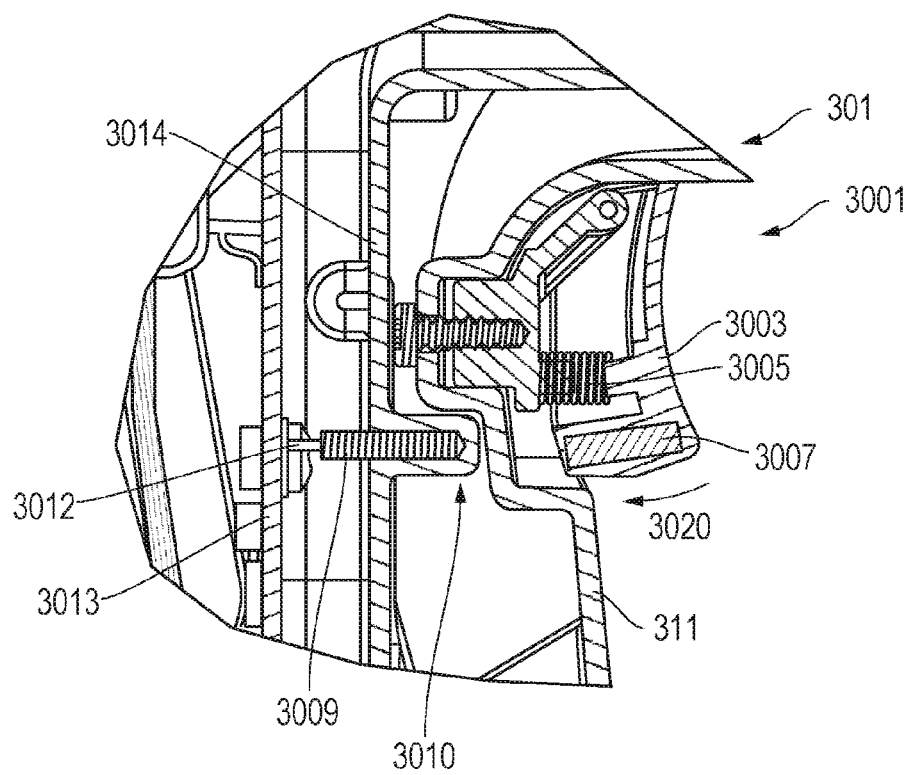
FIG. 28 includes a cross-sectional illustration of a portion of the tool including the trigger according to an embodiment.

FIG. 28 includes a cross-sectional illustration of a portion of a tool including a trigger according to an embodiment. As illustrated, the tool includes a trigger 3001 coupled to the housing 301 of the tool, and particularly connected at the handle 311 of the housing 301 in a manner as illustrated in FIGS. 8 and 15. The trigger 3001 can include a moveable trigger portion 3003 that is pivotably coupled to the housing 301 at a pivot point for rocker-type movement of the trigger by a user. Additionally, the trigger 3001 can include a biasing member 3005 for biasing the moveable trigger portion 3003 in a position as illustrated until the trigger 3001 is forcibly urged by a user to be moved in a direction 3020 as indicated.

The trigger 3001 can also include a trigger switch 3010 that can include certain components for operation of the tool. According to an embodiment, the trigger switch 30110 can include a magnet 3007 that can be coupled to the moveable trigger portion 3003. In particular, the magnet 3007 call be embedded within the moveable trigger portion 3003, such that the magnet 3007 can be moved with the moveable trigger portion 3003. According to one particular embodiment, the trigger switch 3010 can be a reed switch mechanism.

The trigger switch 3010 can further include a sensor 3009 coupled to the housing 301. In particular instances, the sensor 3009 can be directly coupled to an interior portion of the housing 301, and more particularly, directly connected to and even embedded within an interior wall 3014 of the tool. The sensor can include a magnetically sensitive material, such that it can be magnetically coupled and magnetically decoupled when the magnet 3007 is at a certain distance from the sensor 3009. The sensor 3009 further includes an electrical connection 3012, such as a wire, for electrical coupling of the sensor 3009 to a circuit board 3013 that can be contained and sealed within the housing 301.

During operation, a user can move the moveable trigger portion 3003 of the trigger 3001 in a direction 3020 as illustrated from a first position, where it may be naturally biased (i.e., a resting position), to a second position such that the trigger 3001 is in a depressed state. In the resting position, the magnet 3007 can be at a sufficient distance that it is magnetically decoupled from the sensor 3009. As such, the switch 3010 can be in an off state. In moving the moveable trigger portion 3003 to the second position in the direction 3020, the magnet 3007 can be moved to a position that is at a sufficient distance to magnetically couple the magnetically sensitive material contained within the sensor 3009 and the magnet 3007. When the moveable trigger portion 3003 is moved sufficiently to magnetically coupled the magnet 3007 and the sensor 3009, the trigger switch 3010 can be changed from the off state to an on state. As will be appreciated, when the moveable trigger portion 3003 is moved sufficiently, in a direction opposite the direction 3020, such as when a user releases pressure from the moveable trigger portion 3003, the magnet 3007 can be magnetically decoupled from the sensor 3009 and the trigger switch 3010 can be changed from an on state to an off state.

In such conditions wherein the trigger switch 3010 is in an on state, the motor can be in an operable mode, such that the output shaft 315 can be rotated. In particular instances, when the trigger switch 3010 is in an on state, an electrical circuit can be formed between the trigger switch 3010 and the motor 407. Formation of an electrical circuit between the trigger switch 3010 and the motor 407 can be a condition sufficient for operation of the tool, and particularly the rotation of the output shaft 315. In particular embodiments, multiple conditions may be needed for operation of the tool. That is, actuation of the trigger 3001 to turn the trigger switch 3010 to an on state may be one of a plurality of conditions that may need to be met before the tool is in an operable state and the output shaft 315 can be rotated. For example, a clutching switch may also be actuated to a proper state (i.e., an on state) in conjunction with the operation of the trigger switch 3010 for operation of the tool as described herein.

Figure 29:
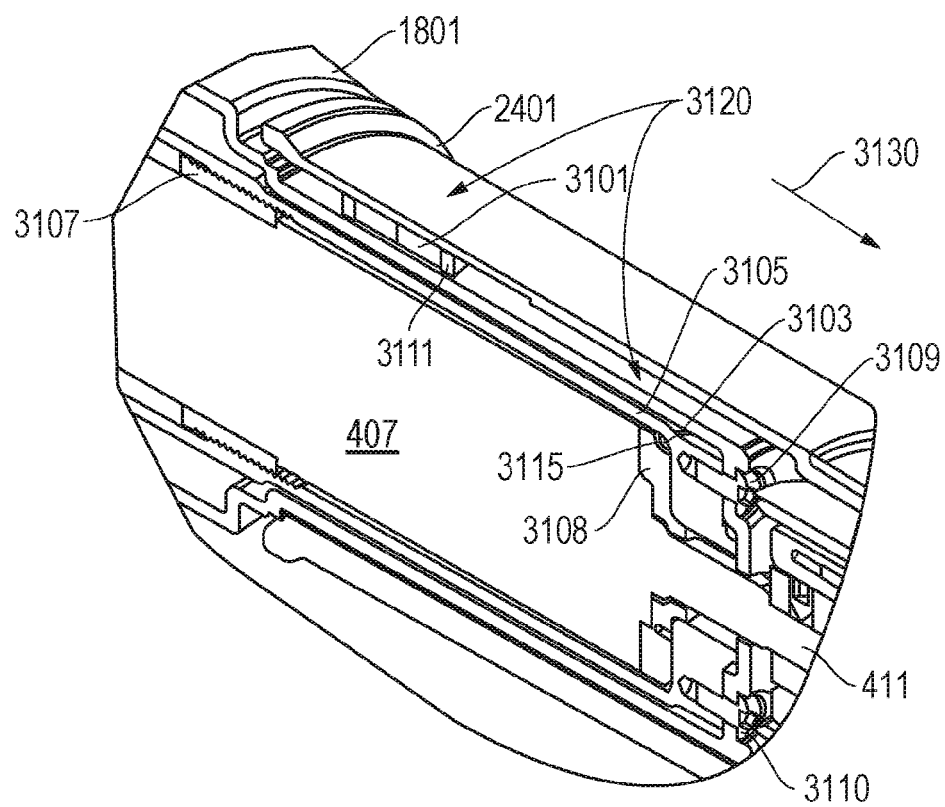
FIG. 29 includes a perspective view illustration of a portion of the tool including the outer sleeve and associated components according to an embodiment.

FIG. 29 includes a perspective view illustration of a cross-section of a portion of a tool including the outer sleeve and associated components in accordance with an embodiment. In particular, certain of the foregoing embodiments have described clutching mechanisms for operation of the tool, such as an actuator arm 2106 and clutching switch 2211. According to other designs, the tool can utilize other mechanisms for operation, and more particularly, clutching of the tool from an off state to and on state using magnetic switching devices.

FIG. 29 illustrates a portion of the tool including the motor 407 and a motor shaft 411 that extends from the motor 407 as described herein. The design of the tool further includes a motor cover 3105 overlying and surrounding the motor 407. The motor cover 3105 can include seals, such that the motor 407 is contained within a sealed environment, which may be particularly suitable for sterilization (e.g., autoclaving) of the tool. The motor cover 3105 and the motor 407 can be connected to each other via a threaded connection 3107 as illustrated. Other suitable fastening mechanism may be employed.

The tool can further include an inner sleeve 1801 coupled to the housing 301 and an outer sleeve 2401 coupled to the housing 301, wherein the inner sleeve 1801 and the outer sleeve 2401 can include those features as discussed herein according to other embodiments. The inner sleeve 1801 can be coupled, and more particularly, fastened to the motor cover 3105, via fasteners 3109 arranged at a distal end of the inner sleeve 1801 and motor cover 3105.

A motor housing cap 3108 can be disposed at a distal end of the motor 407 proximate to the motor shaft 411 between the motor 407 and the distal end of the motor cover 3105. The motor housing cap 3108 is contained within the motor cover 3105 and can include an opening 3115 defined between an interior surface of the motor cover 3105 and an external surface of the motor housing cap 3108. According to particular embodiments, the opening 3115 can be of sufficient size for a sensor 3103 to be seated therein.

The tool can further include a switch 3120 within the housing 301. The switch 3120 can include multiple components, including a sensor 3103 and a magnet 3101 that can be contained within the housing 301 of the tool. In certain designs, the sensor 3103 can be disposed in a position, such that it is spaced apart from the magnet 3103, for example, within the opening 3114 of the motor housing cap 3108. The magnet 3101 can be contained within a retaining ring 3111 and coupled to a different portion of the housing 301 displaced at a suitable distance from the sensor 3103. For example, in some designs, the magnet 3101 and the retaining ring 3111 can be coupled to, and more particularly, directly connected to, an inner surface of the outer sleeve 3401 such that the components are configured to be moveable with the movement of the outer sleeve 2401. In particular instances, the switch 3120 can be a reed switch for controlling the operation of the motor 407.

During operation, the outer sleeve 2401 can be moved from a first position to a second position in a direction 3130, such that it is translated along the inner sleeve 1801 toward the distal end of the tool in manner described in FIGS. 27A and 27B. In the first position, the magnet 3101 is sufficiently spaced apart from the sensor 3103, which contains a magnetically sensitive material, such that the sensor 3103 and the magnet 3101 are magnetically decoupled. When the sensor 3103 and the magnet 3101 are magnetically decoupled, the switch 3120 is in an off state. When the outer sleeve 2401 is moved to a second position and translated in a direction 3130, the magnet 3101 can be moved to a position sufficiently proximate to the sensor 3103 to magnetically couple the magnet 3101 and the magnetically sensitive material of the sensor 3103. In such conditions, the switch 3120 can be changed from the off state to an on state. In certain instances, when the switch 3120 is in an on state, the motor 407 can be placed in an operable mode, wherein the motor shaft 411 can be rotated. In the on state, the switch 3120 may be electrically connected to the motor 407 or associated electronics (e.g., a circuit board) controlling the motor 407.

It will be appreciated that when the switch 3120 is placed in an on state, such a condition may be one of a plurality of conditions that need to be satisfied for operation of the tool. For example, according to certain embodiments, the switch 3120 can be considered a clutching switch, suitable for placing the motor 407 in a ready state, such that in conjunction with the trigger switch 3010 being placed in an on state, the tool can be operated and the output shaft is in a rotateable state (i.e., it can be rotated).

Figure 30:
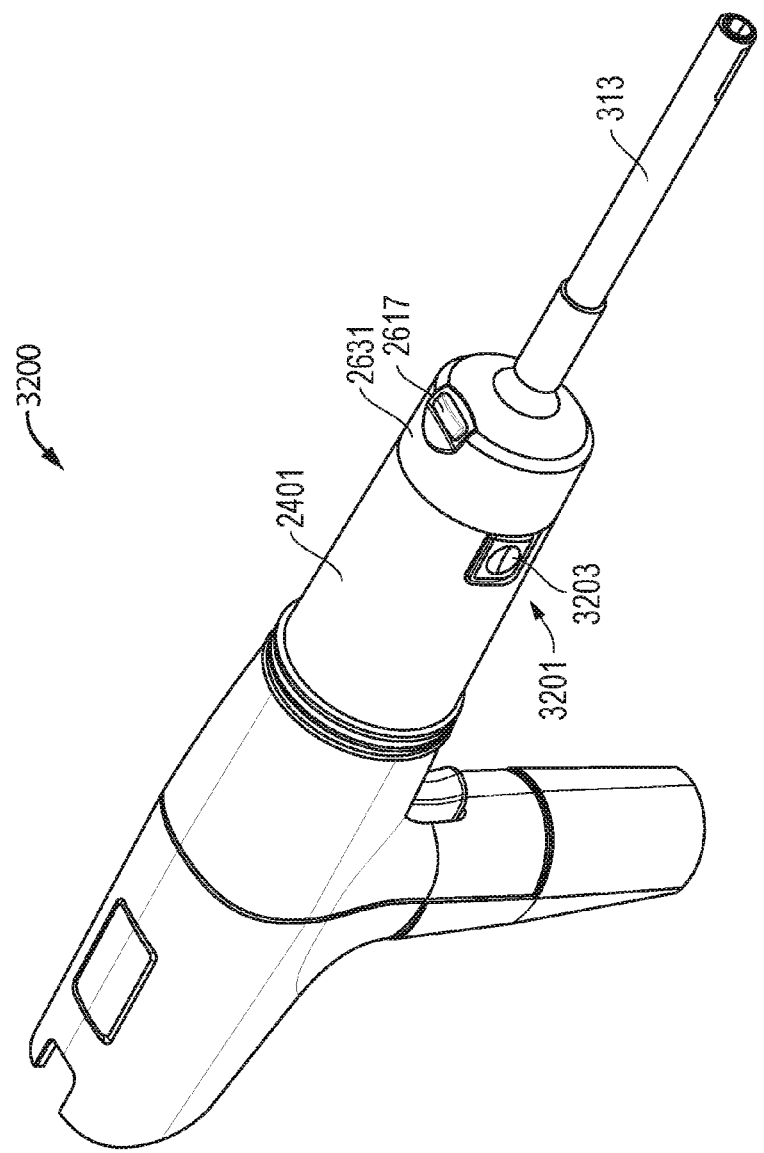
FIG. 30 includes a perspective view illustration of the tool including particular release mechanisms according to an embodiment.

FIG. 30 includes a perspective view of a tool according to one embodiment. In particular, the tool 3200 includes a particular release mechanism 3201 to facilitate removal of the coupling portion 2631 from the housing 301, and more particularly from the outer sleeve 2401. Such removal can facilitate sterilization of the components of the tool and simple assembly and/or disassembly. As further illustrated and described herein, the tool can further be disassembled, by operation of the projection 2617 which actuates the locking member 2613 for releasable engagement of the counter-torque sleeve 313 from the coupling portion 2631. This may be completed before removal of the coupling portion 2631 from the housing 301.

Figure 31:
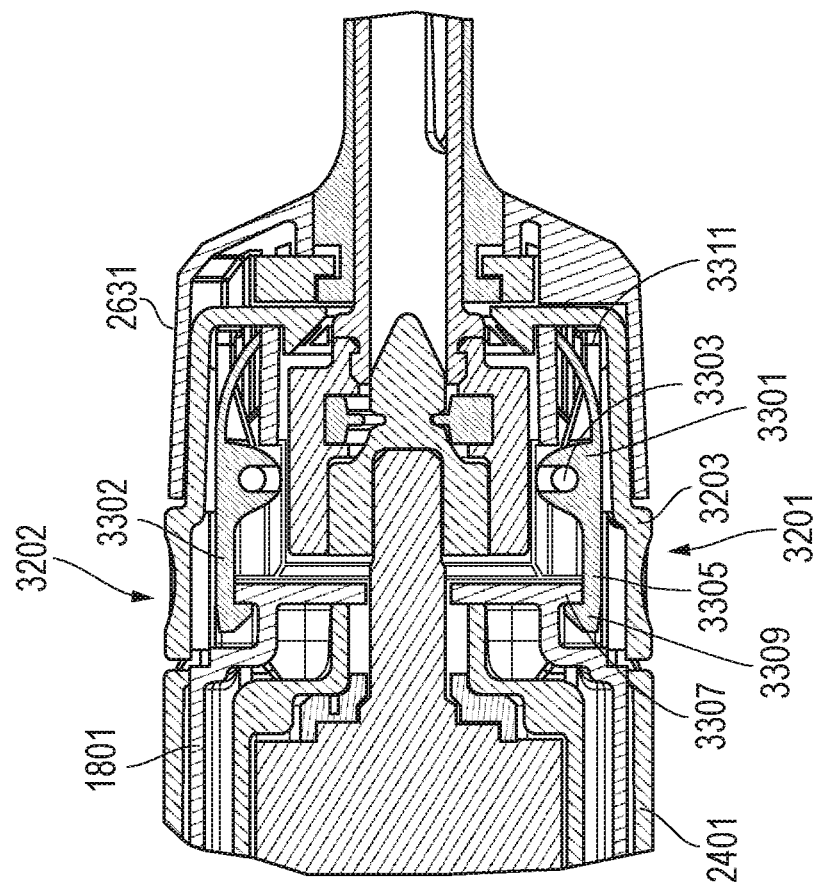
FIG. 31 includes a cross-sectional illustration of a portion of the tool including a release mechanism according to an embodiment.
Figure 32:
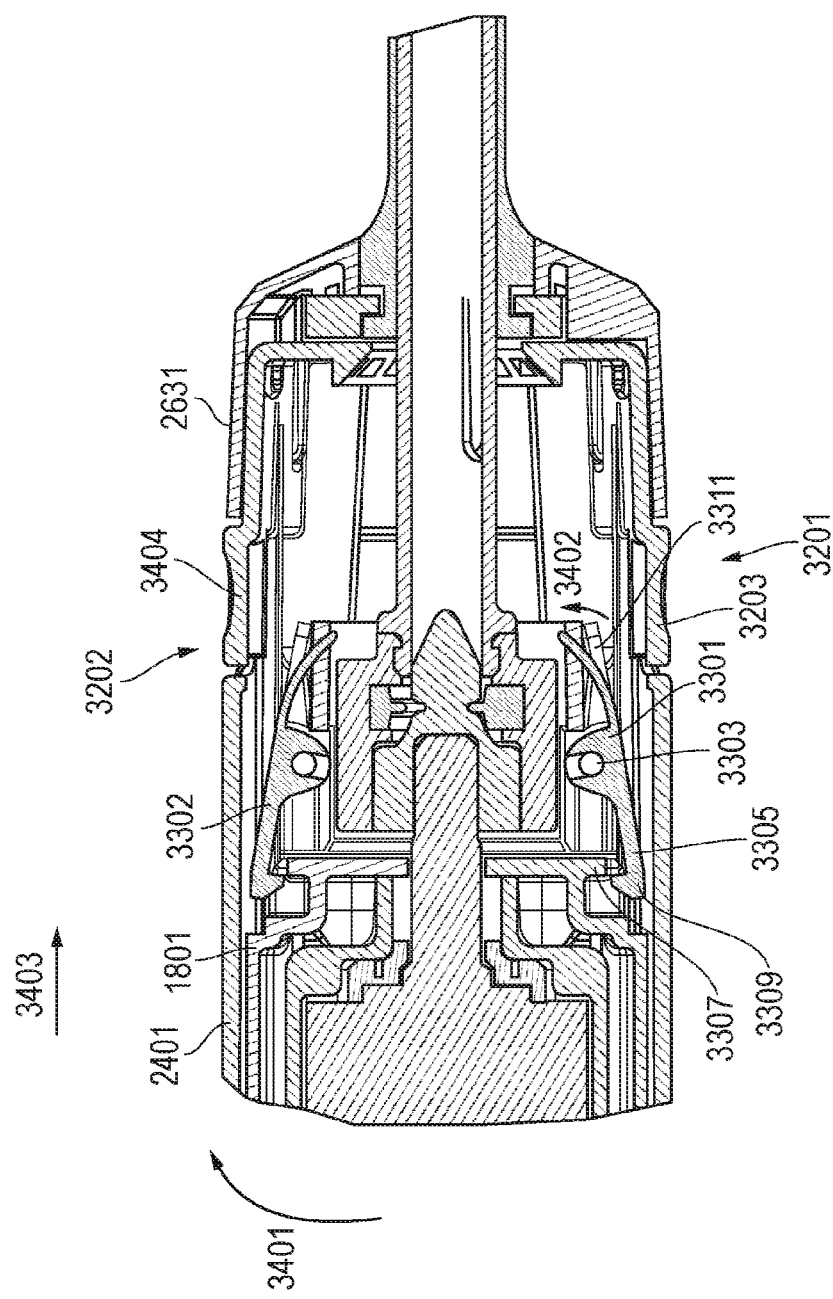
FIG. 32 includes a cross-sectional illustration of a portion of the tool including a release mechanism according to an embodiment.

FIGS. 31-32 include cross-sectional illustrations of portions of the tool including the release mechanism. In particular, FIGS. 31-32 demonstrate the operation of a release mechanism for selective attachment of the coupling portion 2631 with the housing 301 of the tool.

FIG. 31 includes a cross-sectional illustration of a portion of the tool including the release mechanism in accordance with an embodiment. FIG. 31 illustrates the coupling portion 2631 attached to the housing 301 of the tool body in a latched position such that the coupling portion 2631 is affixed and locked in position relative to the housing 301. As illustrated, the release mechanism 3201 can include a button 3203 that can be actuated (e.g., depressed) and moved relative to the housing 301 of the tool to move a portion of a moveable member 3301 contained within the housing 301, which in turn can facilitate removal of the coupling portion 2631 from the outer sleeve 2401. In particular, the moveable member 3301 coupled to the button 3203 can include an arm 3305 having a flange 3309 affixed to an end of the arm 3305 for engagement with a protrusion 3307 at a surface the inner sleeve 1801. The moveable member 3301 can further include an arm 3311 extending from the body of the moveable member 3301 in a direction opposite the arm 3305. The moveable member 3301 can be pivotable around a pivot point 3303 during operation of the button 3203 that results in actuation of the moveable members 3301 and 3302.

As illustrated, the tool can include more than one release mechanism, a first release mechanism 3201 on a first side of the housing 301 and a second release mechanism 3202 on an opposite side of the housing 301. This design can avoid accidental decoupling of the coupling portion 2631 from the housing 301, such that both of the release mechanisms 3201 and 3202 must be actuated in order to remove the coupling portion 2631 from the housing. It will be appreciated that description with regard to the operation of the release mechanism 3201 will be the same as the operation of the release mechanism 3202.

FIG. 31 illustrates the coupling portion 2631 in a latched position wherein the coupling portion 2631 is fixably attached to the housing by virtue of an engagement between the flange 3309 of the arm 3305 and the protrusion 3307 of the inner sleeve 1801. The latched position is suitable when the tool is in use such that the components are fixably attached to each other.

Turning to FIG. 32, the coupling portion 2631 is illustrated in a released position. In certain designs, to change the coupling portion from the latched position (illustrated in FIG. 31) to the released position, the outer sleeve 2401 can be changed from the active groove 2005 to the inactive groove 2003. Such a change can facilitate fuller movement of the outer sleeve 2401 on the inner sleeve 1801. The changing of position of the outer sleeve 2401 can include rotation of the outer sleeve 2401 in a counter-clockwise direction 3401 as illustrated (as held by a user with the distal end of the tool facing away from the user) and can further include translation of the outer sleeve 2401 toward the distal end of the tool in the direction 3403 as illustrated.

Upon placement of the outer sleeve 2401 relative to the inner sleeve 1801 as illustrated in FIG. 32, the release mechanisms 3201 and 3202 can be actuated to change the positions of the associated moveable members 3301 and 3302, respectively. In particular, a user can depress the button 3203, which can contact the arm 3311 of the moveable member 3301, thus displacing the position of the moveable member as it rotates about the pivot point 3303. The inside surface of the button 3203 can contact the arm 3311 and move it in a direction 3402 away from the inner surface of the button 3203 and urging the moveable member 3301 to pivot around its pivot point 3303 such that the flange 3309 of the arm 3305 is decoupled from the protrusion 3307. In this state as illustrated in FIG. 32, the coupling portion 2631 is in a released position and can be decoupled from the housing 301 by translating the coupling portion 2631 in the direction 3403 while holding the outer sleeve 2401 in the same position.

As will be appreciated, when reattaching the coupling portion 2631 to the housing 301, the outer sleeve 2401 can be moved back to the active groove 2005, such that the coupling portion 2631 can be engaged on the housing 301. In particular, reattachment of the coupling portion 2631 can include translating the coupling portion 2631 in a direction opposite the direction 3403 until the inner surface of the button 3203 engages the surface of the arm 3305 (the same applies for the other release mechanism 3202) and pivots the moveable member 3301 back to the position illustrated in FIG. 31, wherein the flange 3309 is engaged with the protrusion 3307.

Figure 33:
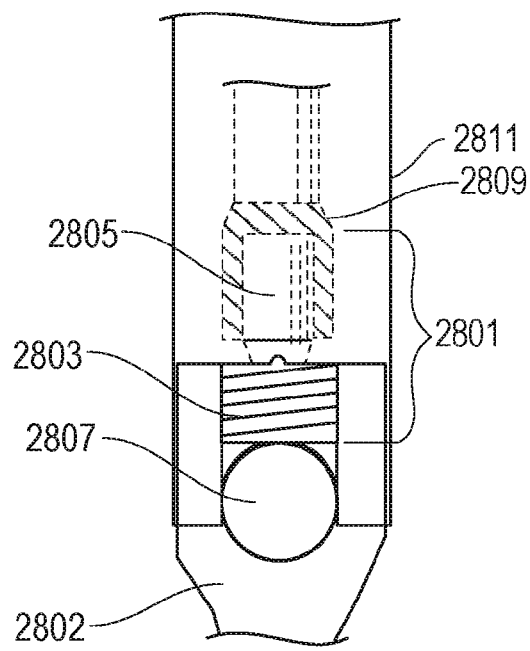
FIGS. 33 and 34 include illustrations of a procedure using the surgical tool to remove a head portion of a set screw in accordance with an embodiment.
Figure 34:
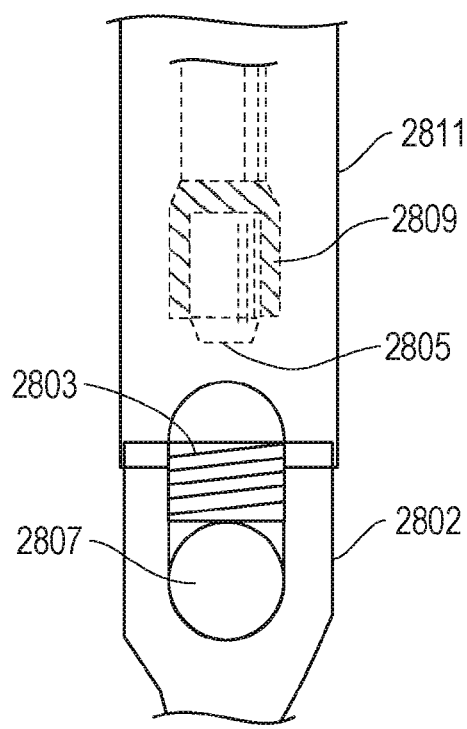

Referring to FIGS. 33 and 34, illustrations are provided that demonstrate the use of the surgical tool for removing a head portion of a set screw. Referring to FIG. 33, a screw is illustrated that includes a set screw 2801 and a bone screw 2802. The set screw 2801 includes a cap 2803 and a head portion 2805 attached to the cap 2803. The bone screw 2802 includes an opening within a head portion configured to engage a rod 2807 therein and fix the position of the screw 2800 relative to the rod 2807 as is typical with rod and anchor systems. As further illustrated in accordance with one embodiment, the output shaft 2809 is engaged with the head portion 2805 of the set screw 1801 such that it is substantially seated around the head portion 2805. Additionally, the counter-torque sleeve 2811 is configured to extend over the output shaft 2809, the set screw 2801 including the head portion 2805 and the cap 2803, such that the counter-torque sleeve 2811 engages the rod 2807 and the head portion of the bone screw 2802. Notably, the output shaft 2809 and the counter-torque sleeve 2811 engage different portions of the implant.

Accordingly, the output shaft 2809 is configured to provide a rotational force to the head portion 2805, while the counter-torque sleeve 2811 is fixably coupled with the rod 2807 such that it is not free to rotate. The coupling configuration at the implant in conjunction with the output shaft 2809 and the counter-torque sleeve 2811 being coupled at the housing creates a design wherein the rotational forces provided by the output shaft 2809 are balanced by an opposing force of the counter-torque sleeve 2811 at the implant since the two are coupled through the housing.

Referring to FIG. 34 after applying a sufficient rotational force, that is a torsional breaking force to the head portion 2805 via the output shaft 2809 the head portion 2805 can be broken or separated from the cap 2803. Notably during breaking of the head portion 2805 from the cap 2803 the counter-torque sleeve 2811 is fixably engaged with the rod 2807 such that it does not rotate, however rotational forces imparted to the screw by the output shaft 2809 on the head portion 2805 are balanced by the counter-torque sleeve 2811 through the housing. Accordingly, during engagement with the bone screw 2802 and rod 2807, the counter-torque sleeve 2811 is configured to provide a substantially opposite torsional force to the torsional breaking force applied by the output shaft 2809 and substantially fix the position of the bone screw 2802 and rod 2807 relative to the housing of the tool during separating the head portion 2805 from the cap 2803. As such, upon breaking of the head portion 2805 from the cap 2803 the transfer of a sudden release of stored energy to the patient is minimized because of the coupling between the output shaft 2809 and the counter-torque sleeve 2811 with the housing. As a result, jarring of the patient is minimized making the procedure safer and also reducing the likelihood of damage to the implant. Moreover, given the mechanical advantage of using a power tool, the effort expended by the surgeon is substantially less, allowing for a more efficient surgery.

Embodiments provided herein represent a departure from the state of the art. In particular reference to breaking head portions of set screws, the state of the art still includes the use of manual tools often resulting in jarring of the patient and doctor. By contrast, the surgical tool provided herein includes a combination of features making such procedures more efficient and safer. The combination of features include, among other things, use of an output shaft and a counter-torque sleeve coupled to a housing such that the rotational forces generated in the output shaft are balanced in the housing by the counter-torque sleeve. Moreover, other features of the present embodiments include selective coupling and decoupling of the motor shaft with the output shaft, use of a particular axial travel distance, use of electrical power, and certain coupling and clutching mechanisms between the counter-torque sleeve as well as the output shaft thereby facilitating a power tool capable of reducing potential injuries to patients during surgery and making surgeries more efficient and less vigorous on surgeons.

In accordance with a first aspect of the present disclosure a surgical tool for removing a portion of an implant within a human is provided that includes a housing, a motor contained within the housing and coupled to the housing, and an output shaft having a distal end and a proximal end opposite the distal end, wherein the proximal end is coupled to the motor and the distal end has an opening configured to rotateably engage an implant. According to the first aspect, the surgical tool further includes a counter-torque sleeve extending around the output shaft having a proximal end and a distal end opposite the proximal end, wherein the proximal end is coupled to the housing and the distal end configured to couple to the implant relative to the counter-torque sleeve such that upon a rotational force to the implant, the forces transmitted by the output shaft and the counter-torque sleeve are balanced by the coupling of the output shaft and counter-torque sleeve through the housing.

According to one embodiment of the first aspect, the housing comprises an outer sleeve and the counter-torque sleeve is coupled to the outer sleeve. In a particular embodiment, the outer sleeve is slideably engageable with an inner sleeve. In another embodiment of the first aspect, the counter-torque sleeve is slideably engageable over the output shaft. In a more particular embodiment, the counter-torque sleeve is moveable between a first axial position and a second axial position, wherein in the first axial position the output shaft is decoupled from the motor.

In accordance with another embodiment of the first aspect, the implant includes a set screw having a breakable head portion and the output shaft is configured to fit over the head portion. In a particular embodiment, the implant further comprises a rod engaged within a portion of the bone screw and the counter-torque sleeve is configured to engage a portion of the rod.

According to a second aspect of the present disclosure, a tool for use during surgery includes a housing, a motor disposed within the housing and connected to the housing, and an output shaft having a proximal end and a distal end opposite the proximal end, wherein the proximal end is coupled to the motor and the distal end having an opening to engage an implant within a patient. The tool of the second aspect further includes a counter-torque sleeve having a proximal end and a distal end opposite the proximal end, the counter-torque sleeve coupled to the housing and overlying the output shaft, wherein the distal end includes an opening to engage the implant.

According to one embodiment of the second aspect, the output shaft has an opening at the distal end configured to engage an implant. In a particular embodiment, the output shaft has an opening at the distal end configured to fit over a head portion of a set screw. In a more particular embodiment, the opening at the distal end of the counter-torque sleeve is configured to engage a portion of a rod extending through the head portion of the bone screw.

In accordance with another embodiment of the second aspect, the counter-torque sleeve is slideably engageable with the output shaft along a longitudinal axis defined by a length of the counter-torque sleeve over the output shaft. In another alternative embodiment, the distal end of the counter-torque sleeve comprises a conformable head configured to engage an implant. In a more particular alternative embodiment, the conformable head comprises an array of pins, each of the pins in the array moveable between a first axial position and a second axial position to engage an implant.

In one embodiment of the second aspect, the counter-torque sleeve is rotateable around a longitudinal axis defined by a length of the counter-torque sleeve. In another particular embodiment, the counter-torque sleeve is rotateable by not less than about 20°. In a still more particular embodiment, the counter-torque sleeve is rotateable by not greater than about 90°.

According to another embodiment, the tool further includes a viewing port within the counter-torque sleeve and the output shaft. In another embodiment, the tool further includes a torque limiter coupled to the output shaft within the housing. As such, in a more particular embodiment, the torque limiter comprises a microprocessor electrically coupled to the motor.

In accordance with another embodiment of the second aspect, the surgical tool further comprising a battery pack disposed within the housing and having a passage extending through the battery pack. In a more particular embodiment, the battery pack is abutting a proximal end of the housing. In still another particular embodiment, the battery pack comprises multiple power cells. In a still more particular embodiment, the multiple power cells are arranged around the passage. In another embodiment, the battery pack has a longitudinal axis and a substantially triangular cross-sectional contour including three corners, wherein the power cells are disposed within the corners of the battery pack and the passage extends substantially along the longitudinal axis.

In one certain embodiment of the second aspect, the passage has a generally circular cross-sectional contour including a diameter of at least about 1 mm. In a more particular embodiment, the diameter of the passage is not greater than about 10 mm. In accordance with one embodiment of the second aspect, the tool further includes a sealed compartment within the housing. In a particular embodiment, the sealed compartment includes a portion of the housing containing a battery pack and the motor.

In a certain embodiment of the second aspect, the output shaft has a length of at least about 10 cm. In one embodiment, the output shaft has a length of not greater than about 40 cm. In another embodiment, the output shaft has a diameter of at least about 3 mm. In still yet another embodiment, the counter-torque sleeve has a diameter that is greater than the diameter of the output shaft. In another particular embodiment, the counter-torque sleeve has a length of at least about 15 cm. As such, in a more particular embodiment, the counter-torque sleeve has a length of not greater than about 40 cm.

According to a third aspect of the present disclosure a tool for use during surgery includes a housing, a motor disposed within the housing, a battery disposed within the housing and coupled to the motor, and an output shaft having a proximal end and a distal end opposite the proximal end, wherein the proximal end is coupled to the motor. The tool further includes a counter-torque sleeve coupled to the housing having a proximal end and a distal end opposite the proximal end, wherein the counter-torque sleeve is slideably engageable over the output shaft between a first position and a second position, wherein at the first position of the counter-torque sleeve the output shaft is unpowered, and at the second position of the counter-torque sleeve the output shaft is powered. As such, in one particular embodiment, in the first position of the counter-torque sleeve, the output shaft is decoupled from the motor and thus the output shaft is unpowered. In still another embodiment, at the first position of the counter-torque sleeve, the motor is disengaged from the battery and thus the output shaft is unpowered.

According to one embodiment of the third aspect, the counter-torque sleeve has an axial travel distance and the distance between the first position and the second position is not less than about 50% of the axial travel distance. In another embodiment, the distance between the first position and the second position is not greater than about 90% of the axial travel distance.

In accordance with another embodiment, the tool further includes a trigger moveable between a first position and a second position, wherein at the first position the motor is at an off state and at the second position the motor is at an on state. In a particular embodiment, at the first position of the counter-torque sleeve the motor is at an off state independent of the position of the trigger. In another particular embodiment, the trigger further includes a failsafe switch disposed on the trigger and moveable between an on position and an off position.

In accordance with one embodiment of the third aspect, the tool further includes a trigger coupled to the handle and operable with a first hand of an operator, and a failsafe trigger coupled to the housing, wherein the failsafe trigger is simultaneously operable with the trigger with the first hand of the operator. As such, in another embodiment, the tool further includes a failsafe switch coupled to the housing and moveable between an off position and an on position, wherein the off position is configured to electrically disengage the motor from the battery. In still another embodiment, the tool further includes a failsafe switch coupled to the housing and moveable between an off state and an on state, wherein the off state is configured to disengage the output shaft from the motor.

In another embodiment of the third aspect, the tool further comprising an audible indicator, optical indicator or both coupled to the housing, wherein the audible indicator or optical indicator has a first state corresponding to the first position of the counter-torque sleeve, and a second state corresponding to the second position of the counter-torque sleeve.

According to another aspect of the present disclosure, a tool for use during surgery includes a motor contained within a housing and connected to the housing and an output shaft having a proximal end coupled to the motor and a distal end opposite the proximal end configured to engage a head of a set screw. The tool further includes a counter-torque sleeve coupled to the housing at a proximal end and having a distal end opposite the proximal end configured to fixably engage a portion of an implant adjacent to the head of the screw, and wherein the output shaft is rotated around an axis defined by a length of the output shaft until the head of the screw is separated from a body while the counter-torque sleeve is fixed relative to the implant and head of the screw. In one embodiment, the motor is a DC electric motor.

According to another aspect, a tool for use during surgery includes a motor contained within a housing and connected to the housing, an effector coupled to the motor and configured to provide rotational force to an implant, and a reaction arm coupled to the housing and the implant, the reaction arm configured to react to the rotational force applied to the implant by the effector. In one embodiment, the reaction arm includes a counter-torque sleeve having a proximal end connected to the housing and a distal end configured to engage the implant. In another embodiment, the effector is configured to be coupled to a first portion of an implant and the reaction arm is configured to be coupled to a second portion of the implant, wherein the first portion and the second portion are different portions, and the reaction arm substantially fixes the location of the second portion of the implant relative to the position of the housing. In a particular embodiment, the effector comprises a distal end having an opening configured to engage a set screw, wherein the effector is configured to apply a torsional breaking force to the set screw to separate a head portion of the set screw from a cap portion. In another particular embodiment, the reaction arm is configured to engage a bone screw and rod coupled to the set screw, wherein during engagement with the bone screw and rod, the reaction arm is configured to provide a substantially opposite torsional force to the torsional breaking force applied by the effector and substantially fix the position of the bone screw and rod relative to the housing during separating the head portion from the cap portion.

In an alternative aspect, a surgical tool for removing a portion of an implant within a human includes a housing, a motor contained within the housing and coupled to the housing, and an output shaft having a distal end and a proximal end opposite the distal end, wherein the proximal end is coupled to the motor and the distal end has an opening configured to rotateably engage an implant. The tool further includes a counter-torque sleeve adjacent to the output shaft having a proximal end and a distal end opposite the proximal end, wherein the proximal end is coupled to the housing and the distal end configured to couple to the implant relative to the counter-torque sleeve such that upon a rotational force to the implant the forces transmitted by the output shaft and the counter-torque sleeve are balanced by the coupling of the output shaft and counter-torque sleeve through the housing. The tool further includes an outer sleeve, wherein the counter-torque sleeve is coupled to the outer sleeve. Notably, the outer sleeve is moveable between a first position and a second position, wherein at the first position the motor is off, and the output shaft is not rotateable. At the second position the motor is on, and the output shaft is rotateable. More particularly, at the first position a switch within the housing is at an off state, and at the second position, a switch within the housing is at an on state.

The tool can further include an inner sleeve coupled to the housing and configured to slideably engage an interior surface of the outer sleeve. The inner sleeve extends axially from a proximal end of a handle and can include an actuator arm within the interior that is engageable with a portion of the outer sleeve. As such, in certain instances, moving the outer sleeve from a first position to a second position a portion of the outer sleeve moves the actuator arm from a first position to a second position. Accordingly, in certain embodiments, moving the actuator arm from a first position to a second position changes a state of a switch, wherein the switch is disposed within the inner sleeve. In some embodiments, the switch changes from an open position to a closed position upon moving the actuator arm from a first position to a second position, wherein at the closed position a closed circuit is formed between the switch and the motor. According to one embodiment, the actuator arm is rotated about a longitudinal axis of the actuator arm from the first position to the second position.

According to another embodiment, the inner sleeve comprises a recess and an opening within the recess for engagement of a portion of the actuating arm therein. The opening can extend axially along a longitudinal axis of the inner sleeve from a distal end of the sleeve. In some cases, the recess comprises an active groove and an inactive groove and the opening is disposed in the active groove of the recess. In more particular instances, a fin of the actuation arm is engaged within the opening at a first position. More particularly, the fin of the actuation arm is biased into a position within the opening via a biasing member in contact with the actuation arm. In other embodiments, a cap is engaged within a distal end of the inner sleeve, and wherein the actuator arm is engaged within the cap.

According to one embodiment of one aspect, the inner sleeve comprises a recess extending axially along an exterior surface of the sleeve. In some cases, the inner sleeve comprises a series of recesses extending axially along the exterior surface of the sleeve. In more particular examples, the recess comprises an active groove and an inactive groove, wherein the active groove and inactive groove are different grooves laterally spaced apart from each other within the recess. In some instances, the outer sleeve comprises a protrusion extending from an interior surface of the outer sleeve for engaging the active groove and the inactive groove. In more particular embodiments of an aspect, at the first position the protrusion is engaged within the inactive groove and at the second position the protrusion is engaged within the active groove.

According to another embodiment, the active groove and the inactive groove are separated by a island disposed within the recess between the active groove and inactive groove. For example, island extends axially along a longitudinal axis of the inner sleeve from a distal end of the inner sleeve. In some embodiments, at the second position, the protrusion is abutting the island. Moreover, moving between the first position and the second position includes rotating the outer sleeve with respect to the inner sleeve about a longitudinal axis of the inner sleeve, such as rotating by not greater than about 30 degrees or not greater than about 10 degrees. Additionally, in some cases moving between the first position and the second position further includes translating the outer sleeve in an axial direction with respect to the inner sleeve. For example, translating includes moving the outer sleeve toward the proximal end of the housing relative to the inner sleeve for an engagement distance, wherein the engagement distance is not greater than about 20% or not greater than about 10% of the total length of the inner sleeve.

According to another aspect, a tool for use during surgery includes a housing, a motor disposed within the housing and connected to the housing, and an output shaft having a proximal end and a distal end opposite the proximal end, wherein the proximal end is coupled to the motor and the distal end having an opening to engage an implant within a patient. The tool further includes a counter-torque sleeve having a proximal end and a distal end opposite the proximal end, the counter-torque sleeve coupled to the housing and overlying the output shaft, wherein the distal end includes an opening to engage the implant. According to one embodiment, the tool includes a trigger coupled to a handle, wherein the handle is coupled to the housing, and the trigger is moveable between a first position and a second position, and moving the trigger between the first and second positions changes the state of a trigger switch between a first state and a second state. Moreover, in certain embodiments, at the second state the trigger switch is at a closed position, and wherein at the closed position a closed circuit is formed between the trigger switch and the motor.

According to another embodiment, of the above aspect, the tool includes a clutching mechanism for coupling the motor and the output shaft, wherein the clutching mechanism is a electromechanical mechanism. In one case, the tool includes an outer sleeve moveable between a first position and a second position, wherein movement between the first position and the second position engages the clutching mechanism. For example, in certain instances, movement of the outer sleeve between the first position and the second position moves a clutching switch between an off state and an on state, wherein at the on state of the clutching switch a closed circuit is formed between the clutching switch and the motor. In another embodiment, the motor is electrically connected to a trigger switch and a clutching switch, and wherein, the motor is operable between an on state and an off state, wherein at the on state the motor is operable and at the off state the motor is inoperable. For example, at the on state of the motor, the trigger switch is at an on state and the clutching switch is at an on state. And further for example, at the off state of the motor, one of either of the trigger switch and the clutching switch are at an off state.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A battery pack for a surgical tool comprising:
   a housing with an elongated body and opposing first and second ends, the housing including an elongated shape with a longitudinal axis that extends through the first and second ends, the housing including an interior space between the body and the first and second ends;
   a passage positioned within the interior space of the housing and through the first and second ends, the passage including an exterior wall that segregates the passage from the interior space and an open interior; and
   at least one power cell positioned within the interior space of the housing.

2. The battery pack of claim 1, wherein the passage includes apertures in each of the first and second ends.

3. The battery pack of claim 1, wherein the housing includes a substantially triangular cross-sectional shape with rounded corners and includes three of the power cells.

4. The battery pack of claim 1, wherein the first end includes an endplate and a sidewall that extends outward from one side of the endplate, the sidewall and the housing including the same cross-sectional shape with the sidewall extending over an exterior surface of the housing when the first end is positioned on the housing.

5. The battery pack of claim 1, wherein the at least one power cell includes a plurality, of power cells arranged in a side-by-side configuration with the passage extending through a center of the configuration.

6. The battery pack of claim 1, further comprising a charging member that extends through one of the first and second ends of the housing, the charging member including an elongated shape with a first end positioned at the at least one power cell and a second end located on an exterior of the housing.

7. The battery pack of claim 1, wherein the interior space is completely enclosed by the housing and the passage.

* * * * *

UNITED STATES PATENT AND TRADEMARK OFFICE
CERTIFICATE OF CORRECTION

PATENT NO. : 10,231,761 B2
APPLICATION NO. : 15/160635
DATED : March 19, 2019
INVENTOR(S) : McGahan et al.

It is certified that error appears in the above-identified patent and that said Letters Patent is hereby corrected as shown below:

On the Title Page

Item (71), under "Applicant", in Column 1, Line 1, delete "Inc," and insert -- Inc., --, therefor.

In the Specification

In Column 1, Lines 9-10, delete "2015 which is a continuation-in-part" and insert -- 2015 and Issued U.S. Pat. No. 9,364,720, which is a divisional --, therefor.

In Column 1, Line 31, delete "sclerosis," and insert -- scoliosis, --, therefor.

In Column 2, Line 30, delete "cross-section" and insert -- cross-section view --, therefor.

In Column 3, Line 11, delete "tool" and insert -- surgical tool --, therefor.

In Column 4, Line 32, delete "requiting" and insert -- requiring --, therefor.

In Column 6, Line 45, delete "call be" and insert -- can be --, therefor.

In Column 7, Line 1, delete "fixable" and insert -- fixably --, therefor.

In Column 9, Line 6, delete "6111" and insert -- 611 --, therefor.

In Column 9, Line 13, delete "to the received" and insert -- to be received --, therefor.

In Column 9, Line 42, delete "viewing, port" and insert -- viewing port --, therefor.

In Column 10, Line 14, delete "perspective" and insert -- perspective view --, therefor.

In Column 10, Line 19, delete "engaged" and insert -- engage --, therefor.

Signed and Sealed this
Fourteenth Day of January, 2020

Andrei Iancu
*Director of the United States Patent and Trademark Office*

CERTIFICATE OF CORRECTION (continued)
U.S. Pat. No. 10,231,761 B2

In Column 10, Line 56, delete "are, flexible" and insert -- are flexible --, therefor.

In Column 12, Line 49, delete "engage wherein" and insert -- engage, wherein --, therefor.

In Column 14, Line 18, delete "front the" and insert -- from the --, therefor.

In Column 15, Line 60, delete "align" and insert -- align with --, therefor.

In Column 16, Line 66, delete "a users" and insert -- a user's --, therefor.

In Column 17, Line 5, delete "19111" and insert -- 1911 --, therefor.

In Column 18, Line 65, delete "configured, to be" and insert -- configured to be --, therefor.

In Column 19, Line 21, delete "according, to" and insert -- according to --, therefor.

In Column 20, Line 53, delete "nm greater" and insert -- not greater --, therefor.

In Column 22, Line 3, delete "engaged" and insert -- engage --, therefor.

In Column 22, Line 19, delete "tails 2407." and insert -- rails 2407. --, therefor.

In Column 22, Line 25, delete "tail elements," and insert -- rail elements, --, therefor.

In Column 25, Line 23, delete "30110" and insert -- 3010 --, therefor.

In Column 25, Line 25, delete "call be" and insert -- can be --, therefor.

In Column 34, Line 27, delete "a island" and insert -- an island --, therefor.

In Column 35, Line 1, delete "a electromechanical" and insert -- an electromechanical --, therefor.

In the Claims

In Column 36, Line 21, in Claim 5, delete "plurality, of" and insert -- plurality of --, therefor.